US008988522B2

(12) United States Patent
Schneider et al.

(10) Patent No.: US 8,988,522 B2
(45) Date of Patent: Mar. 24, 2015

(54) VISUAL INSPECTION DEVICE

(71) Applicant: Milwaukee Electric Tool Corporation, Brookfield, WI (US)

(72) Inventors: Scott Schneider, Waukesha, WI (US); Rick Gray, Bothell, WA (US); Raymond Wai-Man Chan, Hong Kong (CN); Desmond Wai-Nang Tse, Hong Kong (CN); Errol John U. Badajos, Hong Kong (CN); Derek Chiu-Hing Chow, Hong Kong (CN); Hugues Marie R. F. Sanoner, Hong Kong (CN); Paul Fry, Sussex, WI (US)

(73) Assignee: Milwaukee Electric Tool Corporation, Brookfield, WI (US)

(*) Notice: Subject to any disclaimer, the term of this patent is extended or adjusted under 35 U.S.C. 154(b) by 0 days.

(21) Appl. No.: 14/182,230

(22) Filed: Feb. 17, 2014

(65) Prior Publication Data

US 2014/0160268 A1 Jun. 12, 2014

Related U.S. Application Data

(63) Continuation of application No. 13/470,824, filed on May 14, 2012, now Pat. No. 8,659,652, which is a continuation of application No. 12/399,755, filed on Mar. 6, 2009, now Pat. No. 8,189,043.

(60) Provisional application No. 61/034,801, filed on Mar. 7, 2008.

(51) Int. Cl.
*H04N 7/18* (2006.01)
*A61B 1/00* (2006.01)
(Continued)

(52) U.S. Cl.
CPC ............ *H04N 7/183* (2013.01); *A61B 1/00124* (2013.01); *G02B 23/2484* (2013.01); *H04N 5/23241* (2013.01)
USPC ............................................ 348/82; 600/127

(58) Field of Classification Search
USPC ......... 600/127, 131, 160, 162, 102, 104, 125; 606/1; 348/82
See application file for complete search history.

(56) References Cited

U.S. PATENT DOCUMENTS 4,788,967 A 12/1988 Ueda
4,825,850 A 5/1989 Opie et al.
(Continued)

FOREIGN PATENT DOCUMENTS

EP 0573158 12/1993
EP 0941691 9/1999
(Continued)

OTHER PUBLICATIONS

Examiner's Report from the United Kingdom Intellectual Property Office for Application No. 1,014,984.7 dated Oct. 19, 2011 (2 pages).
(Continued)

*Primary Examiner* — Le H Luu
(74) *Attorney, Agent, or Firm* — Michael Best & Friedrich LLP

(57) ABSTRACT

A visual inspection device includes a body having a support portion and a grip portion extending from the support portion. The device also includes a flexible cable having a first end portion coupled to the body and a second end portion, and a camera assembly coupled to the second end portion of the flexible cable. The camera assembly includes an image sensor operable to transmit image data through the flexible cable. The device further includes a display supported by the support portion of the body. The display is electrically connected to the flexible cable to display image date from the image sensor. The device is powered by a rechargeable battery pack removably coupled to the body.

20 Claims, 17 Drawing Sheets

(51) Int. Cl.
  *G02B 23/24* (2006.01)
  *H04N 5/232* (2006.01)

(56) References Cited

U.S. PATENT DOCUMENTS

| | | | |
|---|---|---|---|
| 4,858,001 A | 8/1989 | Milbank et al. | |
| 4,880,713 A | 11/1989 | Levine | |
| 5,363,838 A | 11/1994 | George | |
| 5,373,317 A | 12/1994 | Salvati et al. | |
| 5,573,494 A | 11/1996 | Yabe et al. | |
| 5,609,561 A | 3/1997 | Uehara et al. | |
| 5,736,271 A | 4/1998 | Cisar et al. | |
| 5,736,726 A | 4/1998 | Vanhorn et al. | |
| 5,873,814 A | 2/1999 | Adair | |
| 5,899,851 A | 5/1999 | Koninckx | |
| 5,928,137 A | 7/1999 | Green | |
| 5,951,463 A | 9/1999 | Lombardi et al. | |
| 6,001,058 A | 12/1999 | Sano et al. | |
| 6,059,719 A | 5/2000 | Yamamoto et al. | |
| 6,091,453 A | 7/2000 | Coan et al. | |
| 6,106,457 A | 8/2000 | Perkins et al. | |
| 6,120,435 A | 9/2000 | Eino | |
| 6,184,923 B1 | 2/2001 | Miyazaki | |
| 6,221,007 B1* | 4/2001 | Green | 600/160 |
| 6,315,712 B1 | 11/2001 | Rovegno | |
| 6,335,756 B1 | 1/2002 | Hale et al. | |
| 6,369,849 B1 | 4/2002 | Rzyski | |
| 6,381,484 B1 | 4/2002 | Ayanruoh | |
| 6,419,626 B1 | 7/2002 | Yoon | |
| 6,419,627 B1* | 7/2002 | Ben Nun | 600/125 |
| 6,434,507 B1 | 8/2002 | Clayton et al. | |
| 6,501,197 B1 | 12/2002 | Cornog et al. | |
| 6,520,908 B1 | 2/2003 | Ikeda et al. | |
| 6,554,765 B1 | 4/2003 | Yarush et al. | |
| 6,589,163 B2 | 7/2003 | Aizawa et al. | |
| 6,666,818 B2 | 12/2003 | Dhindsa | |
| 6,692,432 B1 | 2/2004 | Yarush et al. | |
| 6,741,286 B2 | 5/2004 | Meek et al. | |
| 6,750,971 B2 | 6/2004 | Overbeck et al. | |
| 6,793,399 B1 | 9/2004 | Nguyen | |
| 6,847,394 B1 | 1/2005 | Hansen et al. | |
| 6,929,600 B2 | 8/2005 | Hill | |
| 6,982,742 B2 | 1/2006 | Adair et al. | |
| 7,022,068 B2 | 4/2006 | Kim et al. | |
| 7,046,270 B2 | 5/2006 | Murata et al. | |
| 7,057,639 B2 | 6/2006 | Spoonhower et al. | |
| 7,097,614 B2 | 8/2006 | Ishizuka | |
| 7,099,078 B2 | 8/2006 | Spencer | |
| 7,108,657 B2 | 9/2006 | Irion et al. | |
| 7,134,993 B2 | 11/2006 | Lia et al. | |
| 7,199,832 B2 | 4/2007 | Oran | |
| 7,212,128 B2 | 5/2007 | Schenker | |
| 7,214,183 B2 | 5/2007 | Miyake | |
| 7,224,769 B2 | 5/2007 | Turner | |
| 7,236,243 B2 | 6/2007 | Beecroft et al. | |
| D559,386 S | 1/2008 | Pease et al. | |
| D560,804 S | 1/2008 | Pease et al. | |
| 7,384,308 B2 | 6/2008 | Boehnlein et al. | |
| 7,404,794 B2 | 7/2008 | Scholly | |
| 7,431,619 B2 | 10/2008 | Boehnlein et al. | |
| 7,435,218 B2 | 10/2008 | Krattiger et al. | |
| 7,442,167 B2 | 10/2008 | Dunki-Jacobs et al. | |
| 7,522,185 B2 | 4/2009 | Suzuki et al. | |
| D594,361 S | 6/2009 | Miller et al. | |
| D594,362 S | 6/2009 | Miller | |
| D621,732 S | 8/2010 | Whitcomb et al. | |
| D621,831 S | 8/2010 | Whitcomb et al. | |
| 8,659,652 B2 | 2/2014 | Schneider et al. | |
| 2003/0016856 A1 | 1/2003 | Walker et al. | |
| 2003/0114839 A1* | 6/2003 | Looper et al. | 606/1 |
| 2004/0054254 A1* | 3/2004 | Miyake | 600/104 |
| 2004/0133075 A1 | 7/2004 | Motoki et al. | 600/131 |
| 2004/0242958 A1* | 12/2004 | Fujikawa et al. | 600/102 |
| 2005/0085690 A1 | 4/2005 | Tien | |
| 2005/0128288 A1 | 6/2005 | Bernstein et al. | |
| 2005/0129108 A1 | 6/2005 | Bendall et al. | |
| 2005/0143626 A1* | 6/2005 | Prescott | 600/162 |
| 2005/0171399 A1 | 8/2005 | Rich et al. | |
| 2005/0177027 A1 | 8/2005 | Hirata | |
| 2006/0004258 A1* | 1/2006 | Sun et al. | 600/160 |
| 2006/0103740 A1 | 5/2006 | Igarashi | |
| 2006/0155168 A1 | 7/2006 | Pease | |
| 2006/0167340 A1* | 7/2006 | Pease et al. | 600/127 |
| 2006/0176321 A1 | 8/2006 | Nakano et al. | |
| 2006/0206007 A1 | 9/2006 | Bala | |
| 2006/0281972 A1 | 12/2006 | Pease et al. | |
| 2007/0032698 A1 | 2/2007 | Uchimura et al. | |
| 2007/0038020 A1 | 2/2007 | Tien | |
| 2007/0049794 A1 | 3/2007 | Glassenberg et al. | |
| 2007/0129604 A1 | 6/2007 | Hatcher et al. | |
| 2007/0156021 A1 | 7/2007 | Morse et al. | |
| 2007/0185379 A1 | 8/2007 | Newman et al. | |
| 2007/0203396 A1 | 8/2007 | McCutcheon et al. | |
| 2007/0225556 A1 | 9/2007 | Ortiz et al. | |
| 2007/0225561 A1 | 9/2007 | Watanabe et al. | |
| 2007/0225931 A1 | 9/2007 | Morse et al. | |
| 2007/0240892 A1 | 10/2007 | Brotto et al. | |
| 2007/0276183 A1 | 11/2007 | Melder | |
| 2008/0009677 A1 | 1/2008 | Shoroji et al. | |
| 2008/0116093 A1 | 5/2008 | Felten et al. | |
| 2008/0152210 A1 | 6/2008 | Bendall | |
| 2008/0158349 A1 | 7/2008 | Miller et al. | |
| 2008/0204553 A1 | 8/2008 | Thompson | |
| 2008/0248673 A1 | 10/2008 | Boehnlein et al. | |
| 2009/0109045 A1 | 4/2009 | Delmonico et al. | |
| 2009/0167851 A1 | 7/2009 | Miller et al. | |
| 2009/0196459 A1 | 8/2009 | Watt et al. | |
| 2009/0198990 A1 | 8/2009 | Watt et al. | |
| 2010/0033563 A1 | 2/2010 | Boehnlein et al. | |
| 2010/0033986 A1 | 2/2010 | Schober et al. | |

FOREIGN PATENT DOCUMENTS

| | | |
|---|---|---|
| WO | 9315648 | 8/1993 |
| WO | 97/15144 | 4/1997 |
| WO | 00/30526 | 6/2000 |

OTHER PUBLICATIONS

Examiner's Report from the United Kingdom Intellectual Property Office for Application No. GB1014984.7 dated Jun. 21, 2011 (2 pages).
International Search Report and Written Opinion for Application No. PCT/US2009/036395 dated May 5, 2009 (14 pages).
Office Action from the Australian Patent Office for Application No. 2009221762 dated Jun. 8, 2012 (2 pages).
Office Action from the United Kingdom Intellectual Property Office for Application No. 1121678.5 dated Jul. 13, 2012 (3 pages).
Chinese Office Action for Application No. CN2009801148145 dated Mar. 18, 2013 (17 pages).
Examiner's Report from the United Kingdom Intellectual Property Office for Application No. 1121678.5 dated Feb. 27, 2012 (5 pages).
Examination Report from the Intellectual Property Office of Great Britain for Application No. GB1212510.05 dated Jan. 24, 2013 (1 page).
Examination Report from the Intellectual Property Office of Great Britain for Application No. GB1212510.05 dated Feb. 26, 2013 (2 pages).
Combined Search and Examination Report from the Intellectual Property Office of Great Britain for Application No. GB1212510.1 dated Oct. 22, 2012 (8 pages).
Examination Report from the Intellectual Property Office of Great Britain for Application No. GB1121678.5 dated Oct. 23, 2012 (1 page).
Examination Report from the Intellectual Property Office of Great Britain for Application No. GB1212510.1 dated Dec. 24, 2012 (3 pages).
Office Action from the Canadian Intellectual Property Office for Application No. 2,717,776 dated Apr. 3, 2013 (2 pages).

* cited by examiner

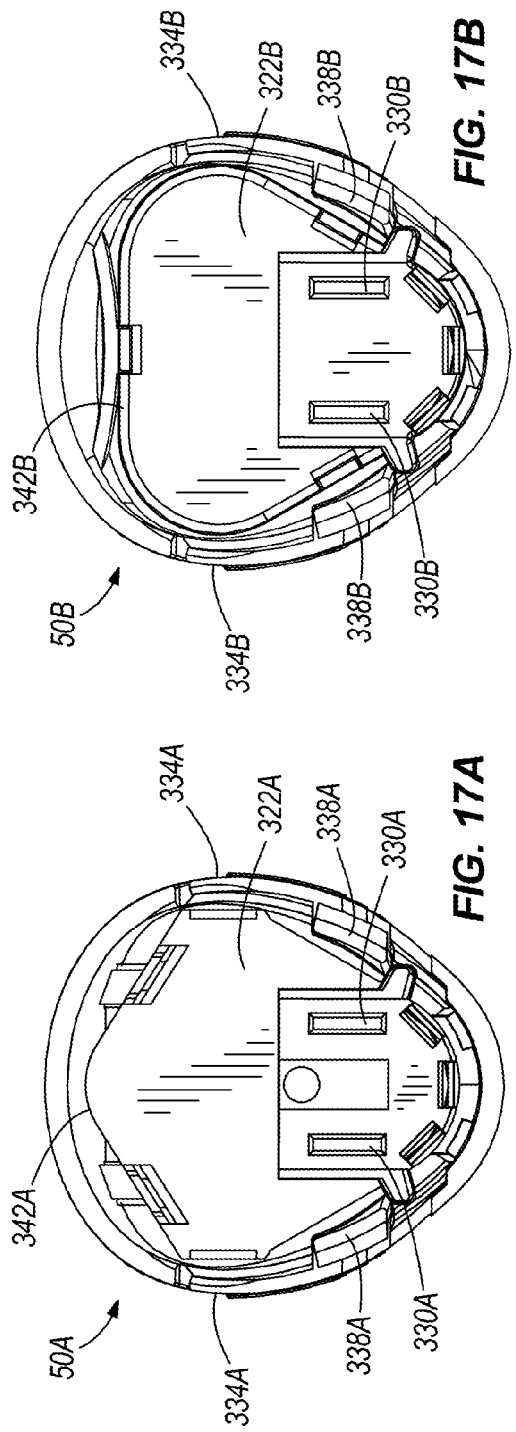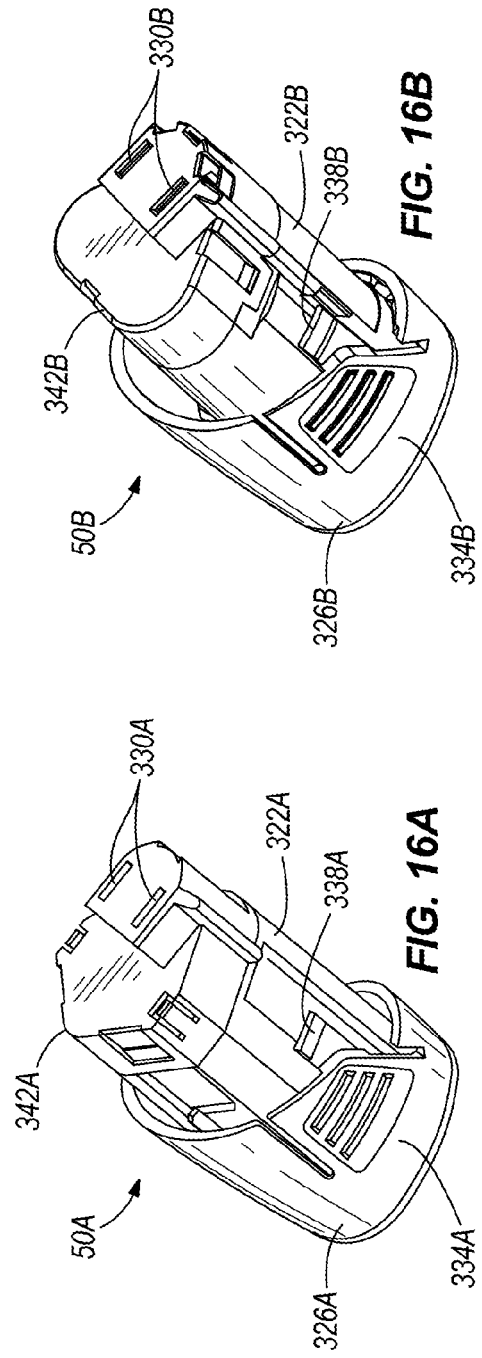

VISUAL INSPECTION DEVICE

CROSS-REFERENCE TO RELATED APPLICATIONS

This application is a continuation of U.S. patent application Ser. No. 13/470,824, filed May 14, 2012, now U.S. Pat. No. 8,659,652, which is a continuation of U.S. patent application Ser. No. 12/399,755, filed Mar. 6, 2009, now U.S. Pat. No. 8,189,043, which claims the benefit of U.S. Provisional Patent Application No. 61/034,801, filed Mar. 7, 2008, the entire contents of both of which are hereby incorporated by reference.

BACKGROUND

The present invention relates to a visual inspection device and, more particularly, to a hand-held visual inspection device for viewing confined or otherwise difficult to access locations.

Visual inspection devices (e.g., borescopes, endoscopes, or the like) provide tradespeople (e.g., plumbers, electricians, mechanics, HVAC (heating, ventilation, and air conditioning) professionals, welders, carpenters, MRO (maintenance, repair, and operations) professionals, or the like) with means to view locations that are inaccessible without dismantling or removing surrounding structures. For example, visual inspection devices are used to inspect inside pipes, walls, floors, aircraft or automobile engines, or other equipment that include narrow, small, and/or dark passageways. Some visual inspection devices have also been employed by surgeons to help view inside patients during, for example, surgery.

SUMMARY

In one embodiment, the invention provides a visual inspection device that includes a body, a flexible cable, a camera assembly, a display, a battery terminal, and a rechargeable battery pack. The body includes a support portion and a grip portion extending from the support portion. The grip portion defines a first axis. The flexible cable includes a first end portion coupled to the body and a second end portion. The first end portion defines a second axis. The camera assembly is coupled to the second end portion of the flexible cable, and the camera assembly includes an image sensor. The image sensor is operable to transmit image data through the flexible cable. The display is supported by the support portion of the body and is electrically connected to the flexible cable to display images captured by the image sensor. The display defines a display plane. The battery terminal is supported by the grip portion, and the battery terminal is electrically connected to at least one of the image sensor and the display. The rechargeable battery pack includes a coupling mechanism that engages the body to releasably secure the battery pack to the body. A portion of the battery pack is engageable with the battery terminal, and the battery terminal is generally exposed when the battery pack is not secured to the body. The first axis intersects the display plane at a first angle, the second axis intersects the first axis at a second angle, the second axis intersects the display plane at a third angle, and the first angle is less than the third angle.

In another embodiment, the invention provides a system of electrical devices that includes a visual inspection device and a removable and rechargeable battery pack. The visual inspection device includes a body, a flexible cable, a camera assembly, a display, and a battery terminal. The body includes a support portion and a grip portion extending from the support portion. The grip portion defines a first axis. The flexible cable includes a first end portion coupled to the body and a second end portion. The first end portion defines a second axis. The camera assembly is coupled to the second end portion of the flexible cable and includes an image sensor. The image sensor is operable to transmit image data through the flexible cable. The display is supported by the support portion of the body and is electrically connected to the flexible cable to display images captured by the image sensor. The display defines a display plane. The battery terminal is electrically connected to at least the display. The first axis intersects the display plane at a first angle, the second axis intersects the first axis at a second angle, the second axis intersects the display plane at a third angle, and the first angle is less than the third angle. The removable and rechargeable battery pack is configured to be coupled to and provide power to the inspection device. The removable and rechargeable battery pack includes a coupling mechanism that engages the body to releasably secure the battery pack to the body, and a portion of the battery pack is engageable with the battery terminal.

Other aspects of the invention will become apparent by consideration of the detailed description and accompanying drawings.

BRIEF DESCRIPTION OF THE DRAWINGS

FIG. 16A is a perspective view of a battery pack for use with the visual inspection device.

FIG. 16B is a perspective view of another battery pack for use with the visual inspection device.

FIG. 17A is an end view of the battery pack of FIG. 16A.

FIG. 17B is an end view of the battery pack of FIG. 16B.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting.

DETAILED DESCRIPTION

Figure 1:
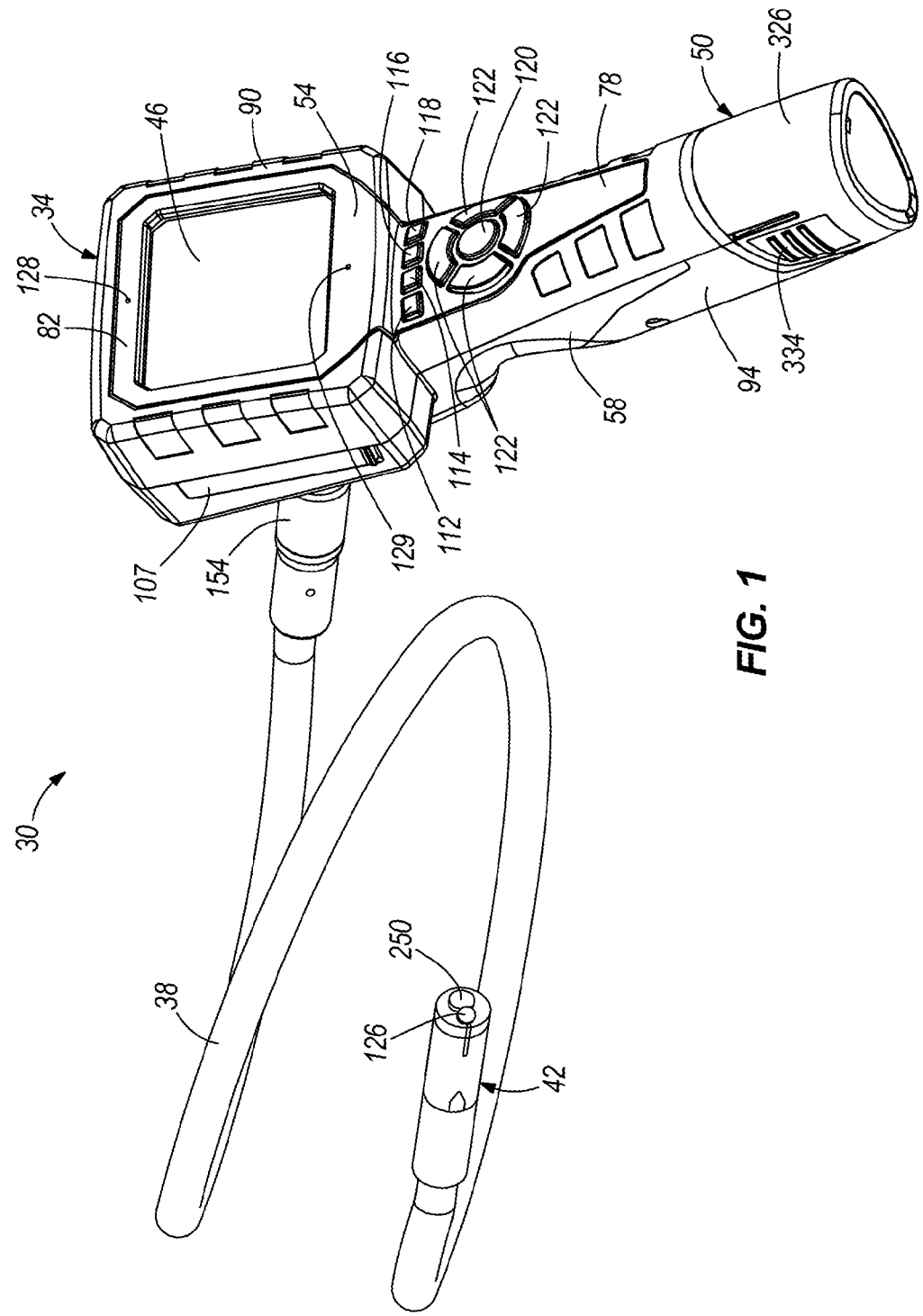
FIG. 1 is a perspective view of a visual inspection device according to one embodiment of the invention.

FIG. 1 illustrates a visual inspection device 30 according to one embodiment of the present invention. In the illustrated embodiment, the visual inspection device 30 is a hand-held unit usable by an operator (e.g., a plumber, an electrician, a mechanic, an HVAC professional, a welder, a carpenter, an MRO professional, or the like) to view the interior of a confined space (e.g., a pipe, a wall, a floor, an engine, or the like). The illustrated visual inspection device 30 includes a body 34, a flexible cable 38 coupled to and extending from the body 34, a camera assembly 42 coupled to the flexible cable 38, and a display 46 supported by the body 34. The visual inspection device 30 also includes a battery pack 50 removably coupled to the body 34.

Figure 2:
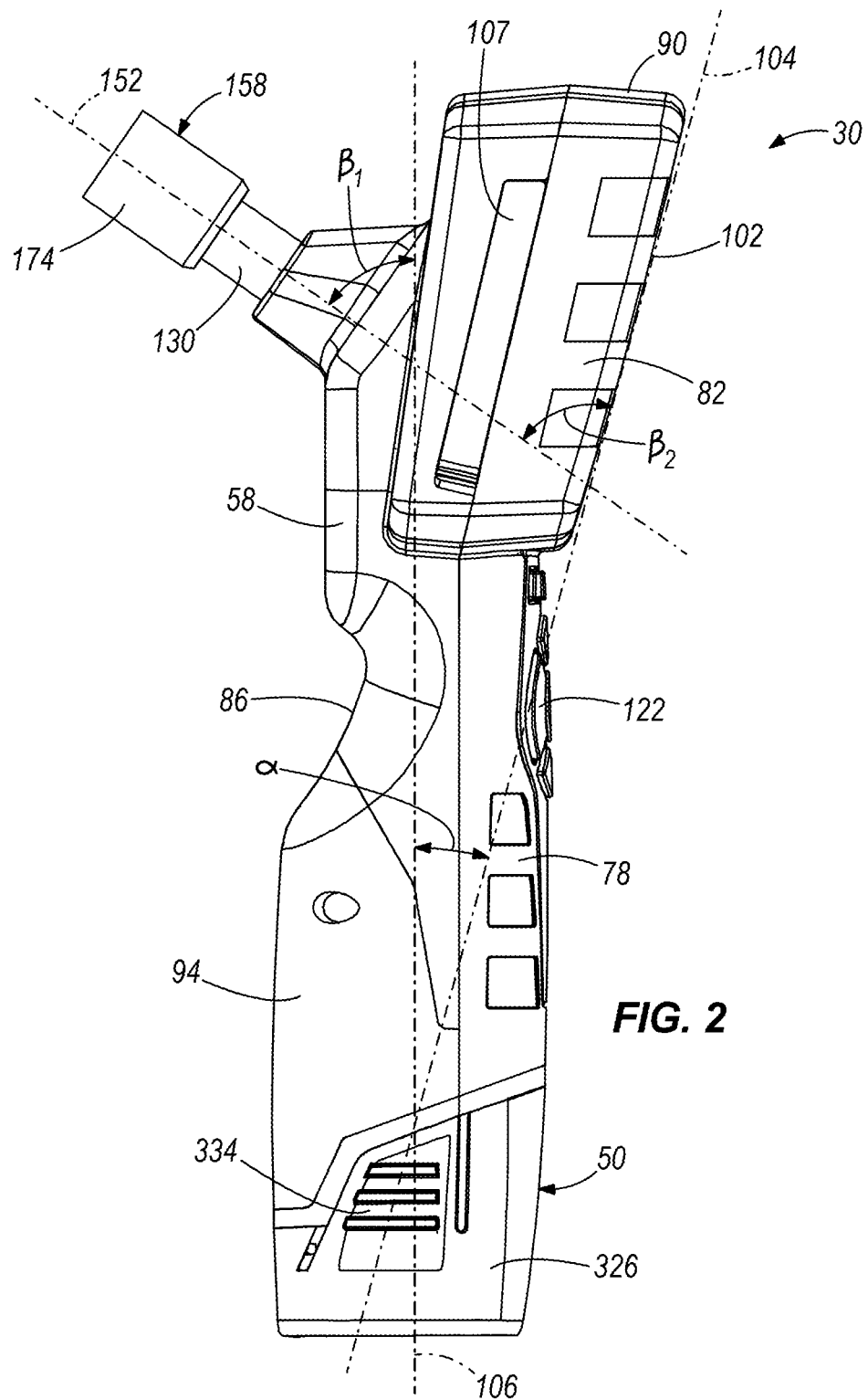
FIG. 2 is a side view of the visual inspection device shown in FIG. 1 without a flexible cable and a camera assembly.
Figure 3:
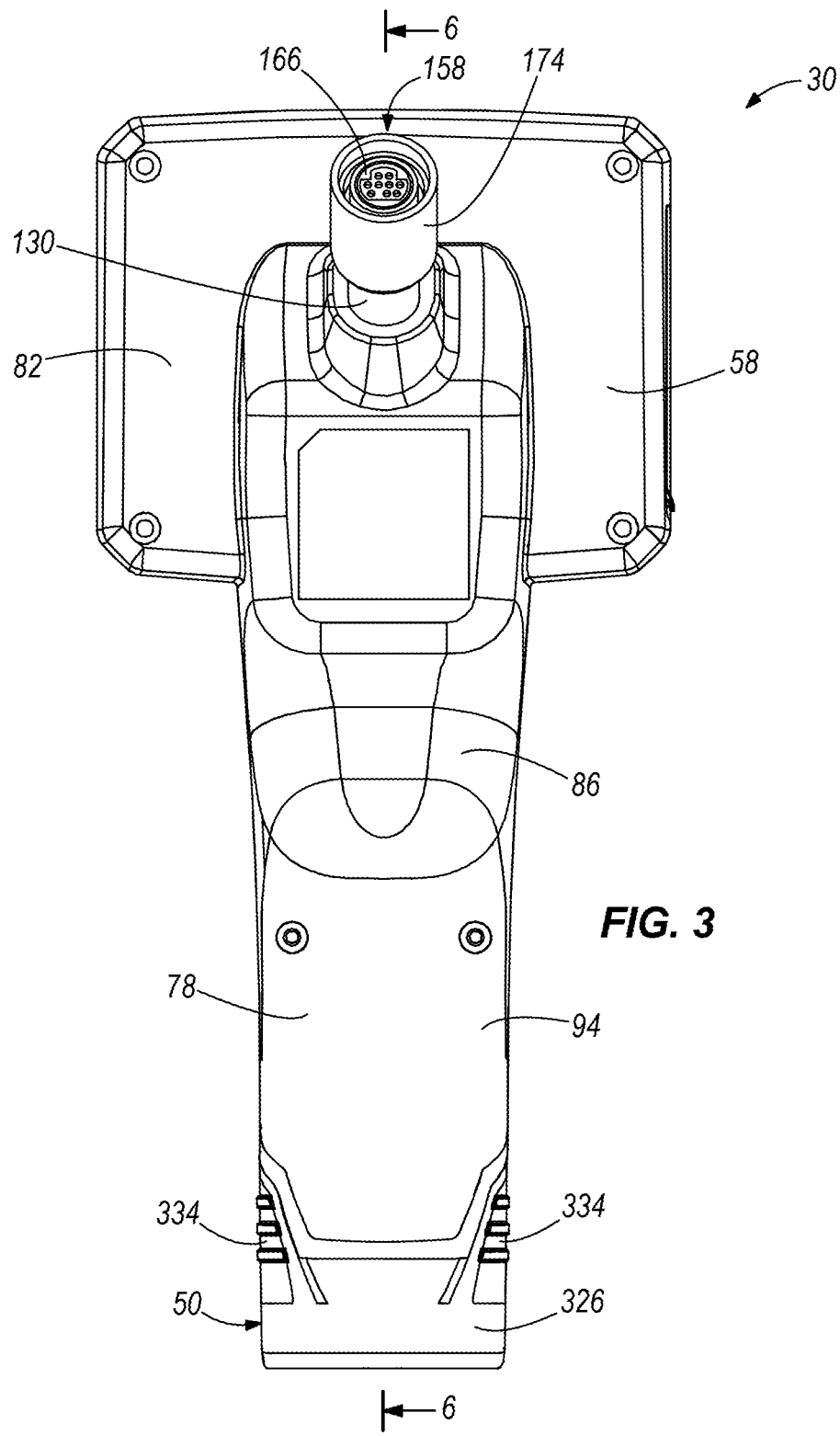
FIG. 3 is a rear view of the visual inspection device of FIG. 2.

Referring to FIGS. 1-6, the body 34 includes an upper housing 54 and a lower housing 58 coupled together in a clamshell manner. The upper housing 54 and the lower housing 58 at least partially enclose and protect the display 46, a display control printed circuit board (PCB) 62, a switch PCB 66, and battery terminals 70. The upper and lower housings 54, 58 define a grip portion 78 configured to be grasped by a user and a support portion 82 configured to support the display 46. As shown in FIGS. 2 and 3, the grip portion 78 includes a contour 86, or recess, formed in the lower housing 58 to facilitate holding the device 30 during operation. An elastomeric overmold 90, 94, or skin, is coupled to each of the upper housing 54 and the lower housing 58 to facilitate gripping of the support portion 82 and to help protect the body 34 if the device 30 is banged into a surface or dropped.

Figure 4:
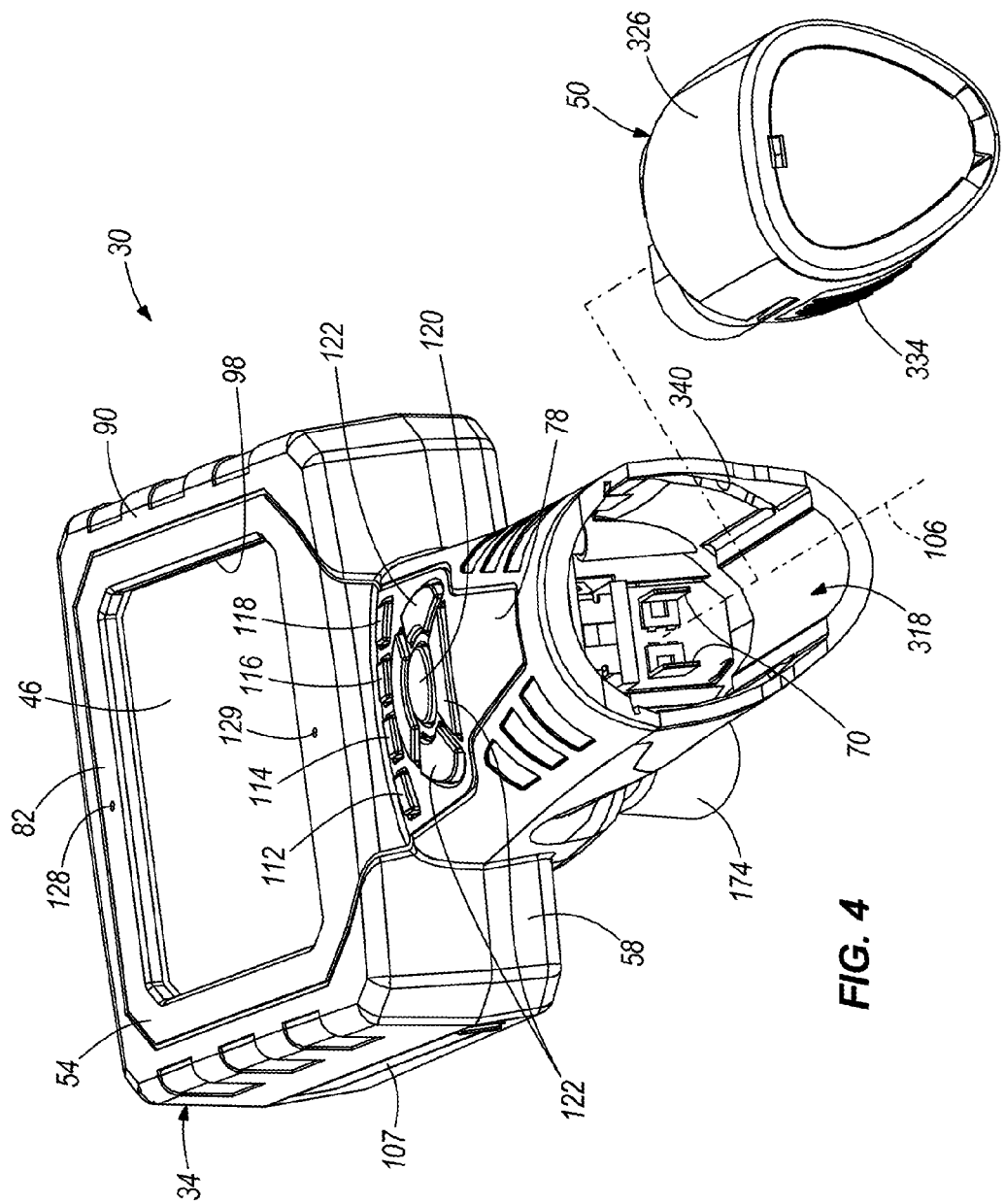
FIG. 4 is an end perspective view of the visual inspection device of FIG. 2 with a battery pack separated from the video inspection device.
Figure 5:
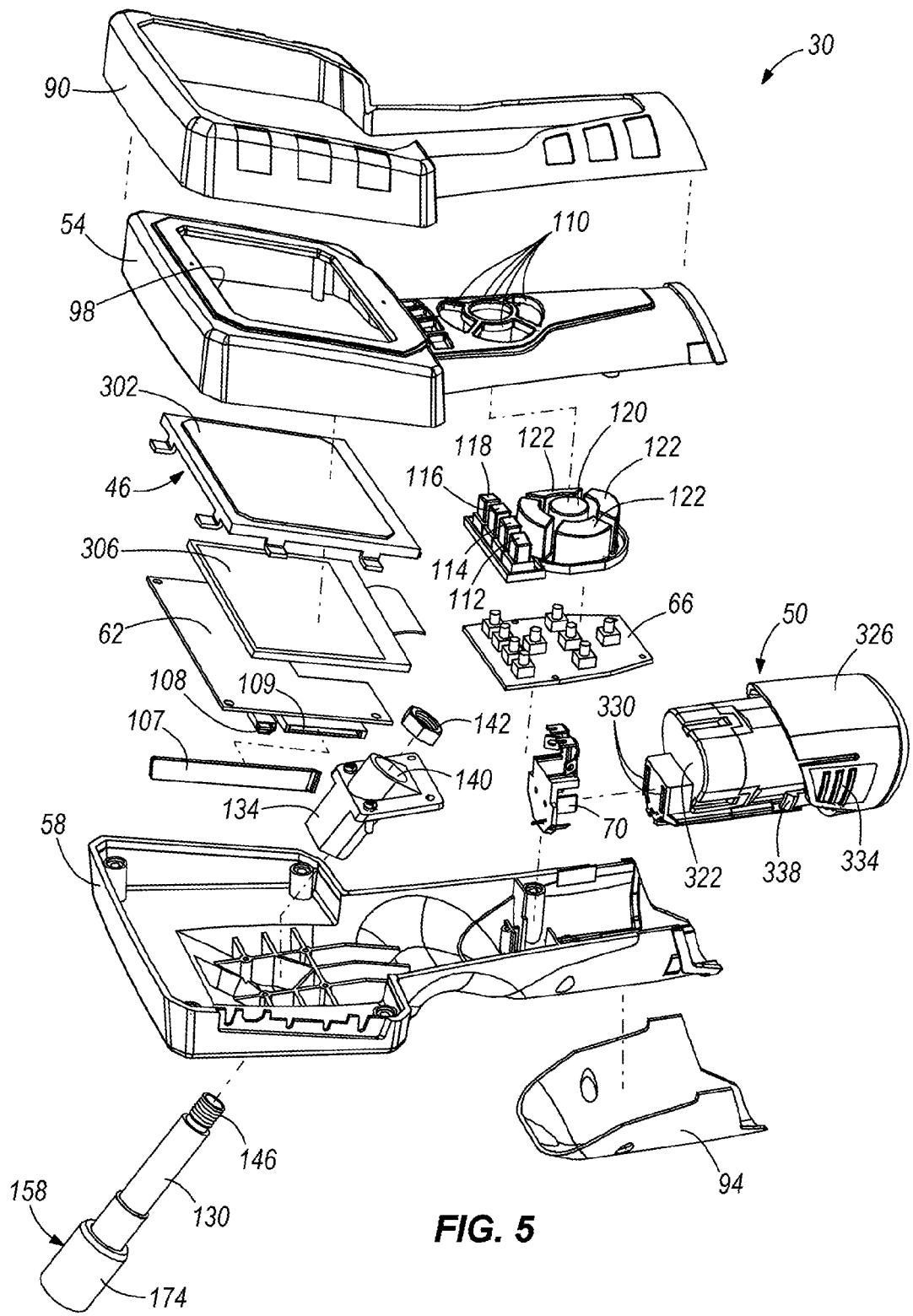
FIG. 5 is an exploded view of the visual inspection device of FIG. 2.

As shown in FIGS. 4 and 5, the support portion 82 defines an opening 98 formed in the upper housing 54. In the illustrated embodiment, the opening 98 is generally square and allows the display 46 positioned within the support portion 82 to be visible through the upper housing 54. In other embodiments, the opening 98 may be rectangular, circular, or the like to complement a shape of the display 46.

As shown in FIG. 2, an upper surface 102 of the support portion 82 defines a display plane 104. The display plane 104 is angled relative to a grip axis 106 extending through the grip portion 78 such that the display 46 is tilted toward the grip portion 78 or actuators 112-122 (described below; i.e., away from the contour 86), and thereby toward a user operating the device 30. The illustrated grip axis 106 extends longitudinally through grip portion 78 from a first end of the grip portion 78 supporting the battery pack 50 to a second end adjacent to the support portion 82. In the illustrated embodiment, the display plane 104 intersects the grip axis 106 at an acute angle α. In some embodiments, the angle α may be between, for example, about 5° and about 25°. Such an orientation facilitates viewing images on the display 46 while holding the device 30 at the grip portion 78. In other embodiments, the support portion 82 may be tilted in the opposite direction such that the display 46 is tilted toward the contour 86 and away from the actuators 112-122.

Referring to FIGS. 1, 2, and 5, the illustrated support portion 82 also includes a cover member 107 (e.g., an elastomeric flap) positioned over an output port 108 (FIG. 5) and a card slot 109 (FIG. 5). The output port 108 and the card slot 109 facilitate connection of removable memory units and other external devices to the device 30. For example, in some embodiments, the output port 108 is a USB port that receives a removable flash drive or a USB cable to connect the device 30 directly to a computer or external monitor. Similarly, in some embodiments, the card slot 109 is configured to receive, for example, a secure digital (SD) card to store images and videos captured by the camera unit 250.

Referring to FIG. 5, the upper housing 54 also defines a plurality of apertures 110 corresponding to a plurality of actuators 112, 114, 116, 118, 120, 122 extending from the switch PCB 66 and out of the housing 54. The illustrated actuators 112-122 are elastomeric buttons used to initiate or control operating functions of the visual inspection device 30. In the illustrated embodiment, the first actuator 112 is a power button to turn the device 300N and OFF, the second actuator 114 is a video button to enter a video mode for recording video clips with the camera assembly 42, the third actuator 116 is a photo button to enter a photo mode for capturing still photos with the camera assembly 42, and the fourth actuator 118 is a playback button to enter a playback mode for displaying the recorded video clips or captured still photos on the display 46. The fifth actuator 120 is a menu or execute button for entering a menu mode of the device 30 and initiating other functions of the device 30. For example, in the menu mode, a user may zoom in or pan across an image, rotate images or videos displayed on the display 46, adjust the brightness or intensity of a light source 126 (FIGS. 12 and 13) in the camera assembly 42, delete or transfer saved data to a remote device, and control various settings of the device 30. The directional buttons 122 surrounding the menu button 120 allow a user to cycle through the different menus and adjust the settings of the device 30 when in a particular mode. In other embodiments, the visual inspection device 30 may include fewer or more actuators operable to control different operating functions of the device 30.

In the illustrated embodiment, the body 34 supports a microphone 128 and a speaker 129. The illustrated microphone 128 is positioned on the support portion 82 adjacent to the display 46. The microphone 128 picks-up and records audio commentary from a user during operation of the device 30. In other embodiments, a microphone may also or alternatively be supported on the camera assembly 42 to pick up audio at a distal end of the cable 38. The speaker 129 is also positioned on the support portion 82, but adjacent to the plurality of actuators 112-122. The speaker 129 outputs the recorded audio from the microphone 128, as well as other instructions, alerts, and warnings preprogrammed into the device 30.

Figure 6:
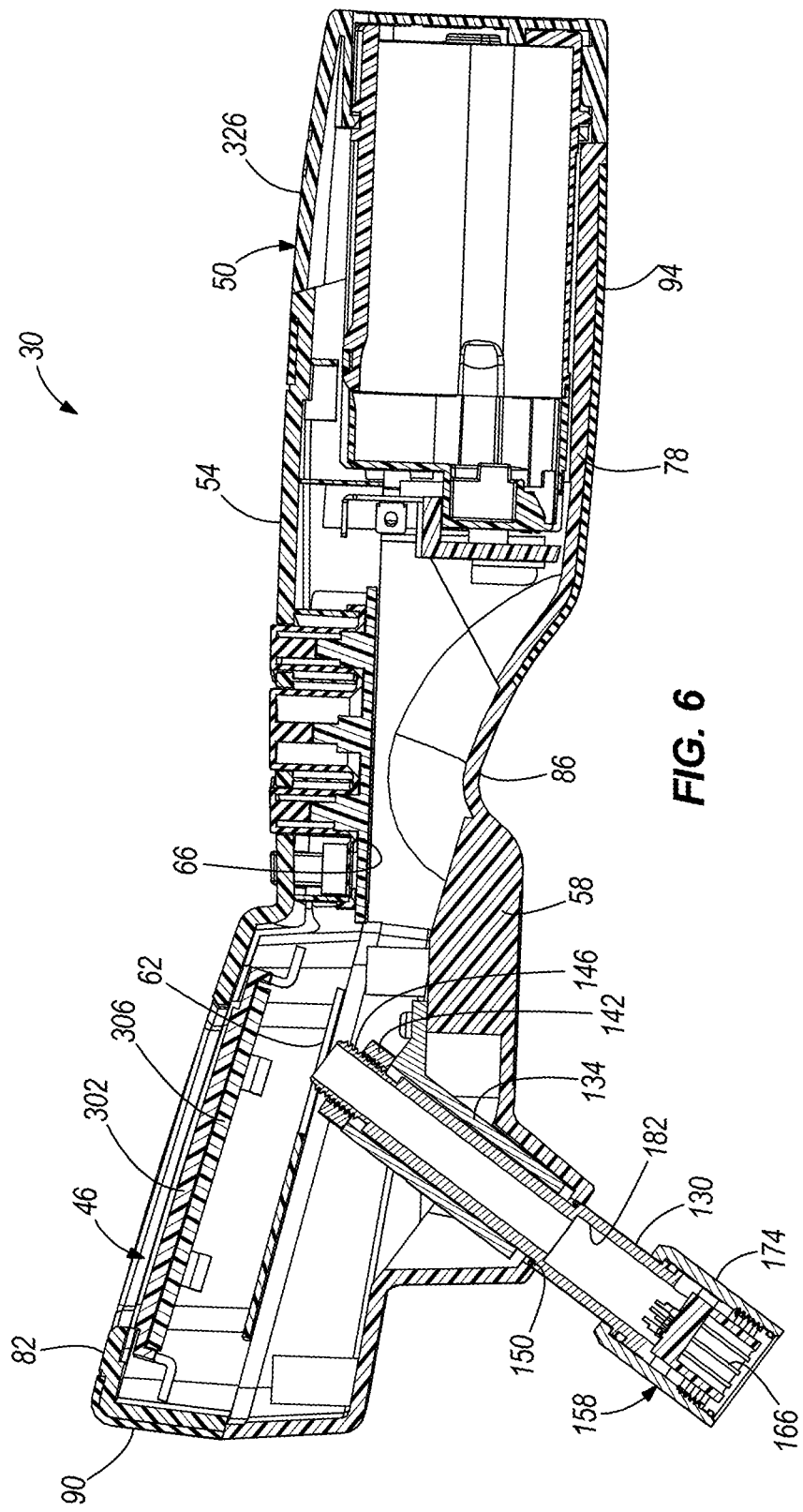
FIG. 6 is a cross-sectional view of the visual inspection device taken along section line 6-6 of FIG. 3.
Figure 7:
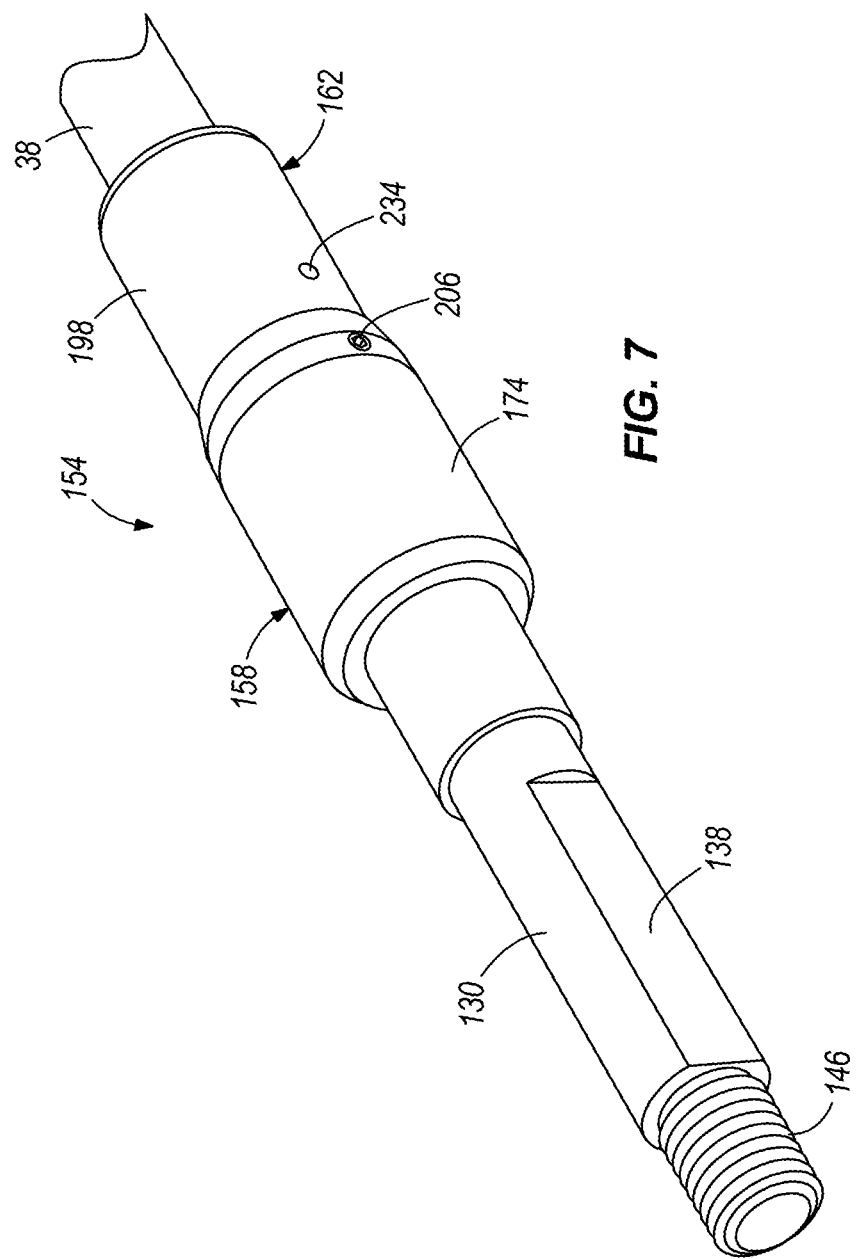
FIG. 7 is a perspective view of a connector assembly for connecting a body of the visual inspection device to the flexible cable.

As shown in FIGS. 5 and 6, the body 34 includes a stem 130 extending from the lower housing 58 and a holder 134 positioned within the body 34 to couple the stem 130 to the lower housing 58. The stem 130 connects to the flexible cable 38 to electrically couple the display 46 and the PCB's 62, 66 to the flexible cable 38 and, thereby, to the camera assembly 42. The holder 134 is securely fastened (e.g., via screws) to the lower housing 58 and receives a portion of the stem 130. The stem 130 includes a flattened surface portion 138 (FIG. 7) corresponding to a D-shaped opening 140 (FIG. 5) in the holder 134 to inhibit rotation of the stem 130 relative to the body 34 and to ensure proper alignment of the stem 130 in the holder 134 during assembly. In the illustrated embodiment, a nut 142 engages a threaded portion 146 of the stem 130 to inhibit the stem 130 from sliding or being pulled out of the holder 134, thereby securing the stem 130 to the body 34. An elastomeric member 150 (e.g., an O-ring) is positioned between the stem 130 and the lower housing 58 adjacent to the holder 134 to help waterproof the body 34.

Referring to FIG. 2, the stem 130 defines a stem axis 152 extending longitudinally through the stem 130. The illustrated stem axis 152 intersects both the grip axis 106 and the display plane 104 at an oblique angle. In particular, the stem axis 152 intersects the grip axis 106 at a first oblique angle $\beta_1$ and intersects the display plane 104 at a second oblique angle $\beta_2$. In the illustrated embodiment, the first angle $\beta_1$ is between about 50° and about 70° and the second angle $\beta_2$ is between about 60° and 80°.

As shown in FIG. 1, the flexible cable 38 is coupled to the stem 130 of the body 34. The flexible cable 38 supports a plurality of wires to electrically couple the display 46 and the PCB's 62, 66 to the camera assembly 42. The illustrated cable 38 is sufficiently rigid to maintain its shape, yet flexible enough to bend around corners and through, for example, pipes where necessary. In some embodiments, such as the illustrated embodiment, the cable 38 is composed of carbon steel and covered or coated with a polyvinyl chloride (PVC) skin to decrease friction between the cable 38 and the surrounding environment (e.g., a pipe surface), as well as to help waterproof the cable 38. In the illustrated embodiment, the flexible cable 38 may be, for example, about three feet or about six feet long. In other embodiments, the flexible cable 38 may be connected to a cable extension to increase the overall length of the cable 38, as further discussed below.

Figure 8:
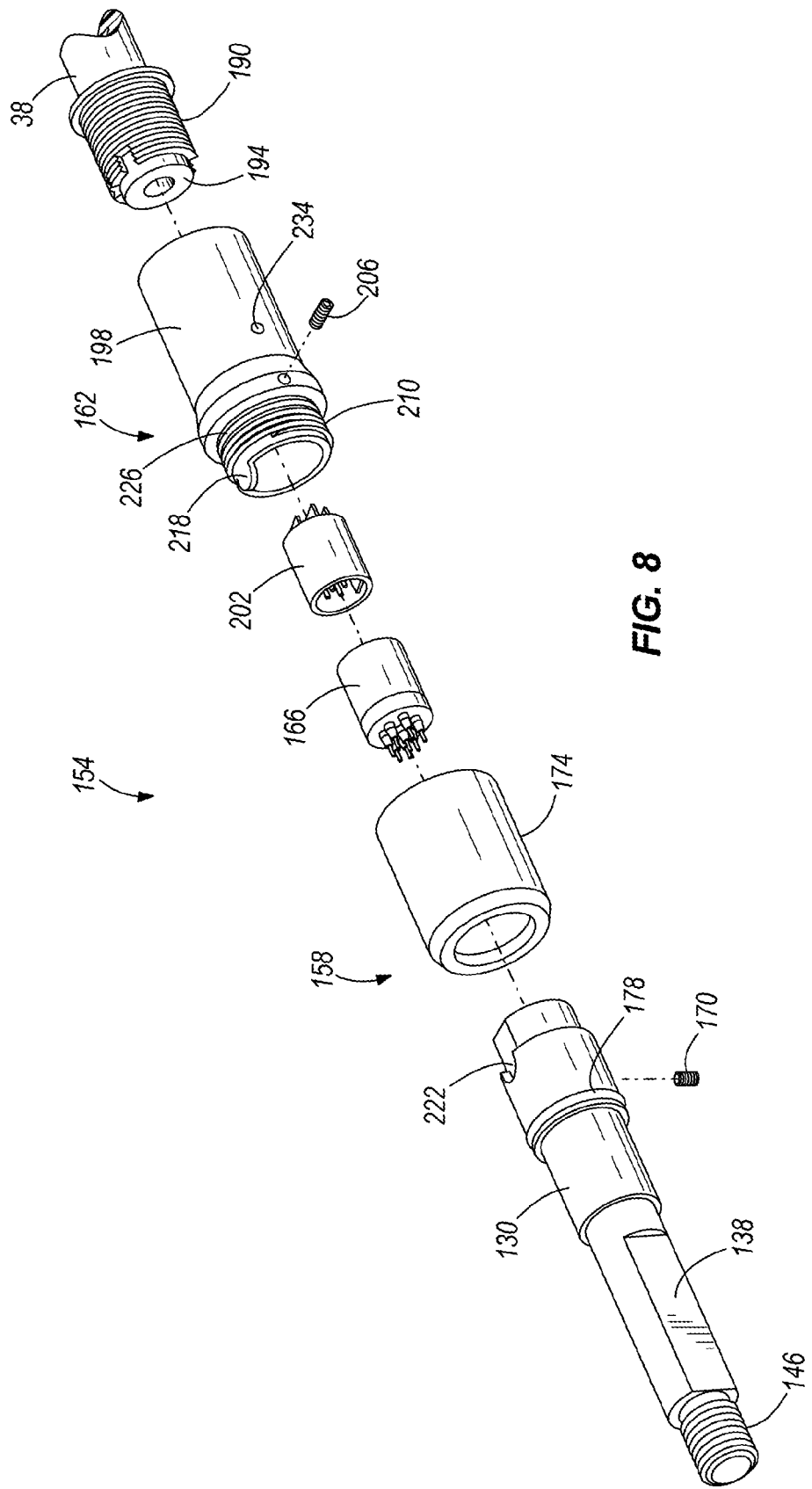
FIG. 8 is an exploded view of the connector assembly of FIG. 7.
Figure 9:
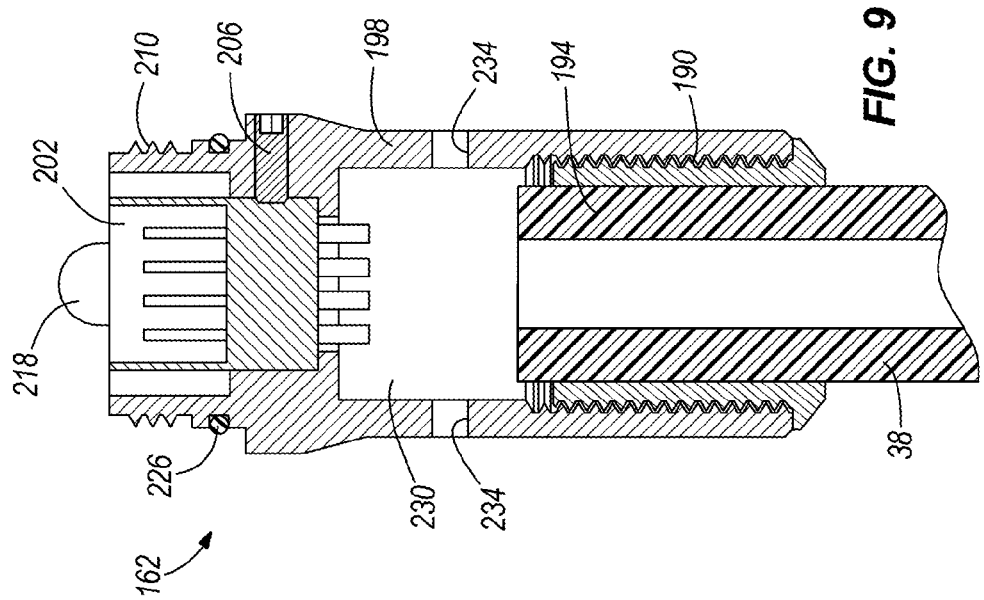
FIG. 9 is a cross-sectional view of a portion of the connector assembly of FIG. 7 connected to the body.

Referring to FIGS. 7-10, a connector assembly 154 releasably couples the flexible cable 38 to the stem 130. The illustrated connector assembly 154 includes a stem connector portion 158 (FIGS. 8 and 9) supported on the stem 130 and a cable connector portion 162 (FIGS. 8 and 10) supported on the flexible cable 38. As shown in FIGS. 8 and 9, the stem connector portion 158 includes an electrical connector 166, or din receptacle, positioned substantially in an end of the stem 130 opposite the threaded portion 146. In the illustrated embodiment, the electrical connector 166 is a 9-pin connector and is secured in place with a set screw 170. The stem connector portion 158 also includes a collar 174, or sleeve, slidably coupled to the stem 130. The collar 174 engages the cable connector portion 162 to securely connect the stem connector portion 158 and the cable connector portion 162 together. An elastomeric member 178 (e.g., an O-ring) is positioned between the stem 130 and the collar 174 to help waterproof the connector assembly 154. In some embodiments, a cavity 182 in the stem 130 may be filled through a port 186 with a potting compound to help waterproof the stem 130 and secure the electrical connector 166 in place.

Figure 10:
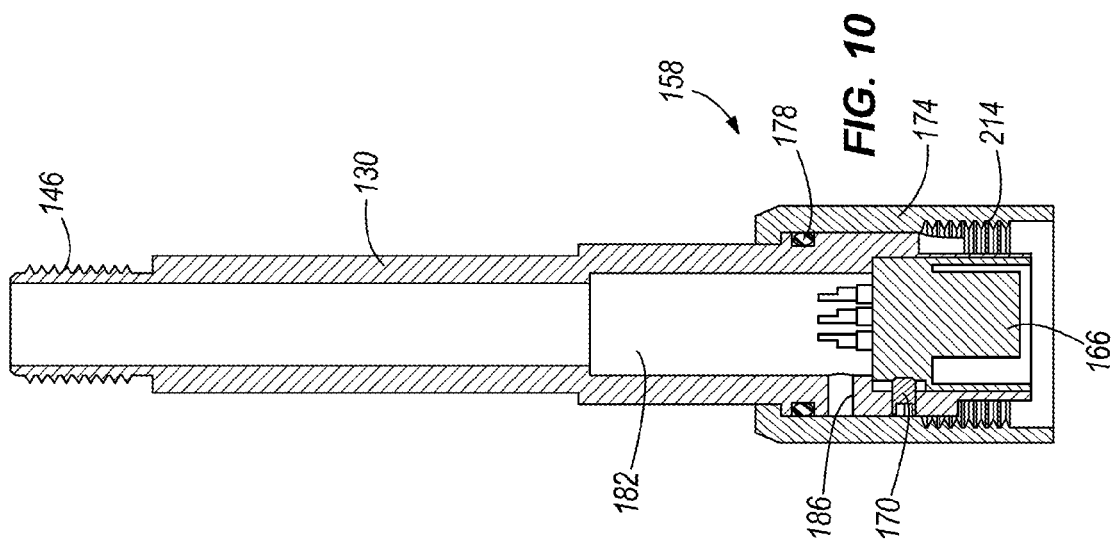
FIG. 10 is a cross-sectional view of a portion of the connector assembly of FIG. 7 connected to the flexible cable.

As shown in FIGS. 8 and 10, the cable connector portion 162 includes an adaptor 190 securely mounted (e.g., press fit) on a first end portion 194 of the cable 38, a plug connector 198 threadably coupled to the adaptor 190, and an electrical connector 202, or din receptacle, positioned substantially within the plug connector 198. The illustrated electrical connector 202 is a 9-pin connector configured to mate with the electrical connector 166 of the stem connector portion 158 and is secured in place with a set screw 206. The illustrated plug connector 198 includes a threaded portion 210 configured to be engaged by a threaded portion 214 of the collar 174 to secure the cable connector portion 162 to the stem connector portion 158. The plug connector 198 also includes a tongue 218 configured to be received in a corresponding recess 222 formed in the stem 130 to inhibit rotation of the cable connector portion 162 relative to the stem connector portion 158. An elastomeric member 226 (e.g., an O-ring) is positioned adjacent to the threaded portion 210 of the plug connector 198 to help waterproof the connector assembly 154. In some embodiments, a cavity 230 in the plug connector 198 between the electrical connector 202 and the cable 38 may be filled through ports 234 with a potting compound to help waterproof the connector assembly 154 and secure the plug connector 198 and the electrical connector 202 in place.

As shown in FIGS. 1 and 11-13, the camera assembly 42 is coupled a second end portion 242 of the flexible cable 38 opposite the connector assembly 154. The illustrated camera assembly 42 includes a generally cylindrical housing 246, a camera unit or image sensor 250, the light source 126, and a lens 254. In the illustrated embodiment, the camera unit 250 and the light source 126 are mounted adjacent to an end of the housing 246 on a first printed circuit board (PCB) 258. A second PCB 262 extends perpendicularly from the first PCB 258 to electrically couple the wires extending through the flexible cable 38 to the camera unit 250 and the light source 126. The illustrated camera unit 250 may be, for example, a CCD (charge coupled device) or a CMOS (complementary metal oxide semiconductor) operable to capture an image and transfer image data through the wires to the display 46. In the illustrated embodiment, the image data is transferred from the camera unit 250 to the display 46 digitally, as further discussed below. Transferring the image data digitally requires less energy and, therefore, increases the runtime of the device 30.

The illustrated light source 126 is a white light emitting diode (LED) extending from the first PCB 258 and beyond the camera unit 250. In other embodiments, the camera assembly 42 may include multiple LED's extending from the PCB 258 and/or may include different types of light sources. The light source 126 provides illumination to an area around the camera unit 250. In the illustrated embodiment, the brightness, or intensity, of the light source 126 is controlled by a user operating the device 30. For example, a setting in the menu mode allows the user to adjust the light intensity between a low, a medium, and a high brightness setting by depressing one or more of the corresponding directional buttons 122 (FIG. 1).

Figure 11:
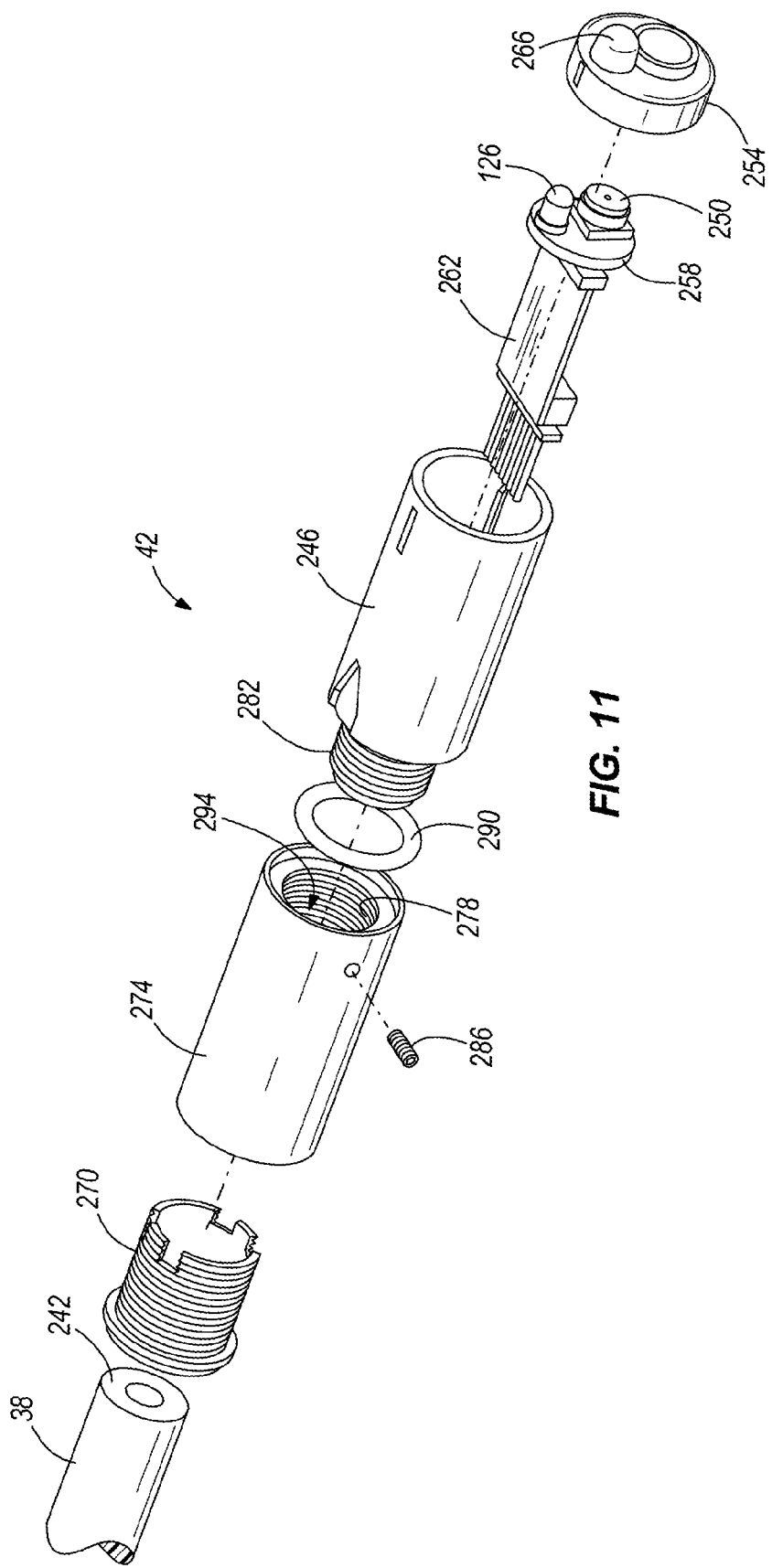
FIG. 11 is an exploded view of a portion of the flexible cable and the camera assembly of the visual inspection device.
Figure 12:
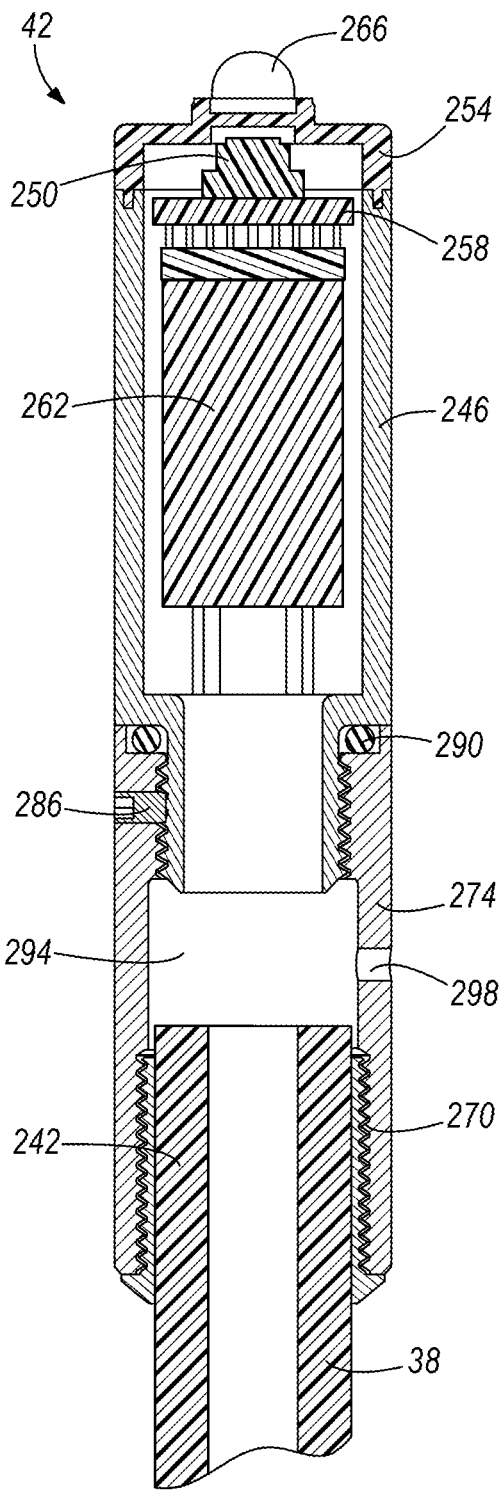
FIG. 12 is a cross-sectional view of the portion of the flexible cable and the camera assembly of FIG. 11.
Figure 13:
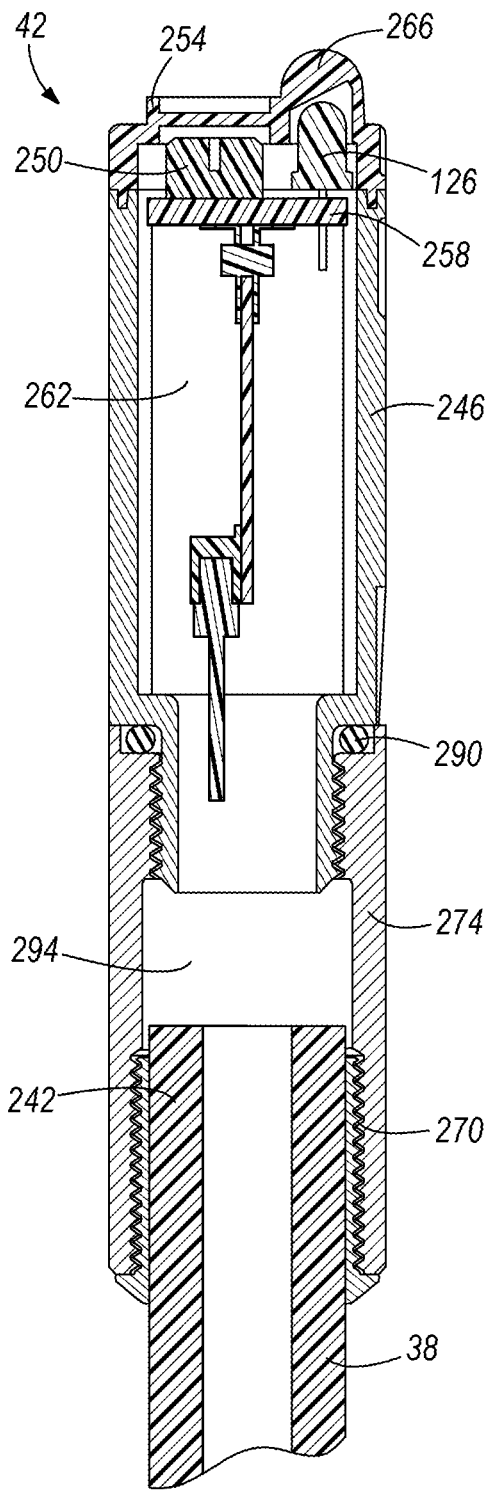
FIG. 13 is another cross-sectional view of the portion of the flexible cable and the camera assembly of FIG. 11.

The lens 254 is coupled to the end of the housing 246 to cover and protect the camera unit 250 and the light source 126. In some embodiments, such as the illustrated embodiment, the lens 254 is ultrasonic welded or brazed to the housing 246. As shown in FIGS. 11-13, the lens 254 includes a protrusion 266 to accommodate the additional height of the light source 126 and to help focus, or direct, the light emitted from the light source 126 to an area of interest adjacent to the camera unit 250.

With continued reference to FIGS. 11-13, the flexible cable 38 includes an adaptor 270 securely mounted (e.g., press fit) on the second end portion 242 of the cable 38 opposite the connector assembly 154 and a camera connector 274 threadably coupled to the adaptor 270. The camera connector 274 includes a threaded portion 278 configured to engage a corresponding threaded portion 282 of the camera housing 246 to secure the camera assembly 42 to the cable 38. A set screw 286 extends through the camera connector 274 to further secure the camera assembly 42 relative to the cable 38. As shown in FIGS. 12 and 13, an elastomeric member 290 (e.g., an O-ring) is positioned between the camera housing 246 and the camera connector 274 adjacent to the threaded portions 278, 282 to help waterproof the camera assembly 42. In some embodiments, a cavity 294 in the camera connector 274 between the housing 246 of the camera assembly 42 and the cable 38 may be filled through a port 298 (FIG. 12) with a potting compound to further help waterproof the camera assembly 42 and to secure the camera assembly 42 to the flexible cable 38.

As shown in FIG. 5, the display 46 includes a lens 302 and a liquid crystal display (LCD) 306 operable to display images captured by the camera unit 250. The display 46 is positioned within the support portion 82 of the body 34 such that the LCD 306 is visible through the opening 98 in the upper housing 54. The lens 302 is positioned within the opening 98 to cover and protect the LCD 306. In the illustrated embodiment, the lens 302 is made of a clear polycarbonate material. The LCD 306 is electrically coupled to the display control unit PCB 62 to receive image data from the camera unit 250. The LCD 306 is also electrically coupled to the switch PCB 66 to receive operating functions initiated by a user (e.g., power ON/OFF, zoom, pan, etc.). Operation of the camera unit 250 and the LCD 306 are discussed in more detail below with reference to FIG. 22.

Figure 15:
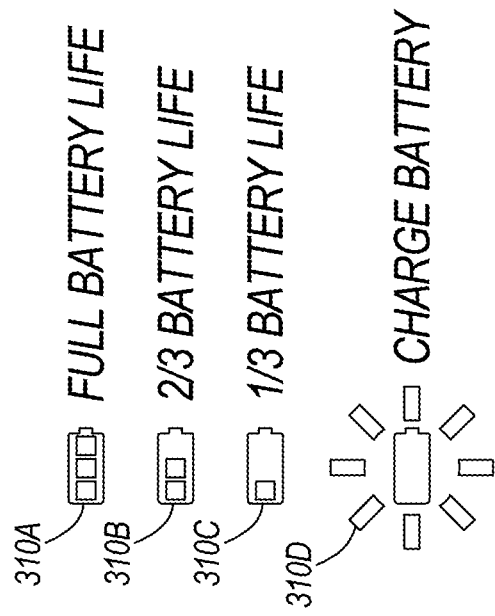
FIG. 15 illustrates a variety of battery life indicia for the display of FIG. 14.
Figure 14:
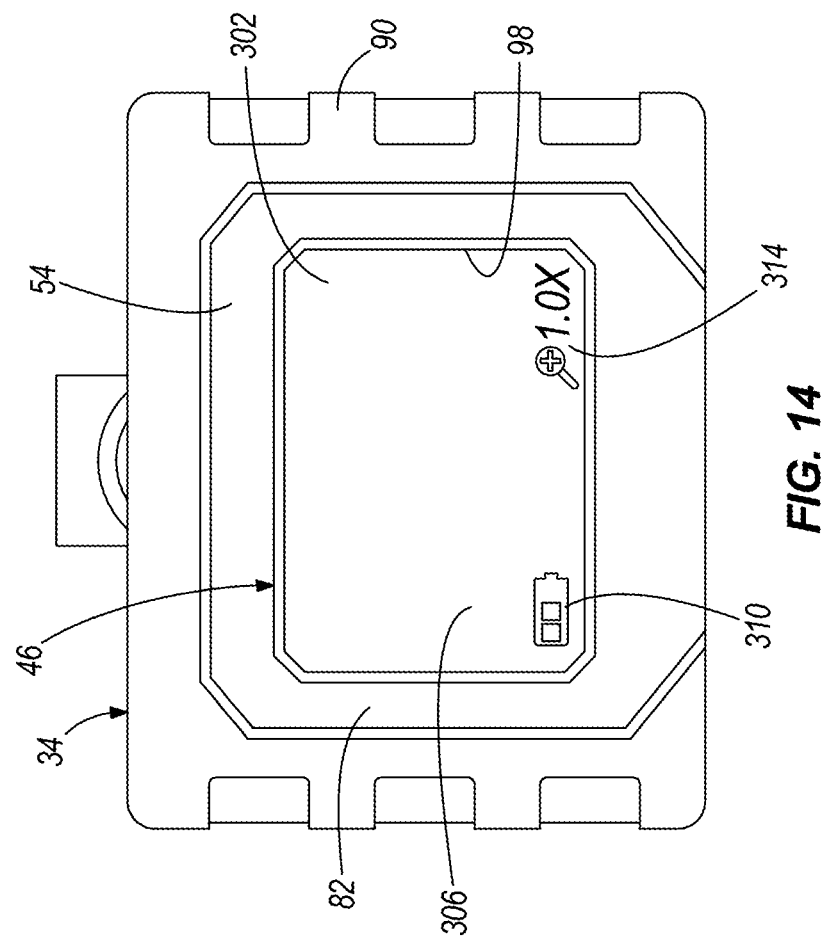
FIG. 14 is a front view of a display and a portion of the body of the visual inspection device.

Referring to FIGS. 14 and 15, the LCD 306 not only displays images from the camera unit 250, but also displays indicia relating to the operation of the visual inspection device 30. For example, as shown in FIG. 14, the LCD 306 displays a battery life indicator 310 and a zoom indicator 314. The battery life indicator 310 helps a user identify approximately how much battery power (e.g., voltage) is left in a battery pack coupled to the device 30. As shown in FIG. 15, the illustrated battery life indicator 310 displays four different indicators relating to four different battery lives (e.g., a full battery life indicator 310A, a ⅔ battery life indicator 310B, a ⅓ battery life indicator 310C, and an empty or charge battery indicator 310D). In some embodiments, the charge battery indicator 310D may blink or flash when displayed. Although not illustrated, the LCD 306 may also display other types of indicia. The illustrated LCD 306 displays a different indicator to notify a user if the device 30 is currently in the video record mode, the still photo mode, or the playback mode. In addition, when the device 30 enters the menu mode, the LCD 306 will display menu identifies relating to the various options and settings available for the device 30. Furthermore, the LCD 306 may also disclose other types of informative indicia, such as the current date and time, the amount of memory left in an internal or removable disk, or the like.

Referring back to FIG. 14, the zoom indicator 314 identifies the current zoom setting on the LCD 306. Actuating (e.g., depressing) the directional buttons 122, when in the proper menu setting, allows a user to change between the various zoom settings. In the illustrated embodiment, the zoom function cycles between 1.0× zoom and 4.0× zoom by 0.1× (i.e., ten percent) increments. In other embodiments, the zoom function may zoom up to, for example, 5.0× or 10.0× zoom, and/or the zoom function may increase and decrease by different increments (e.g., 0.05×, 0.25×, 0.5×, 1.0×, or the like). In the illustrated embodiment, the zoom function digitally zooms in on an image displayed on the LCD 306. In other embodiments, actuating the zoom button 122 may physically alter or adjust the camera unit 250 to zoom in on an area of interest. When zoomed in on an image, the directional buttons 122 also allow a user to pan across the image, when in the proper menu setting.

Referring to FIGS. 1-6, the battery pack 50 is removably coupled to the body 34 to provide power to the camera assembly 42 (e.g., the camera unit 250 and the light source 126), the LCD 306, and the PCB's 62, 66, 258, 262. In the illustrated embodiment, the battery pack 50 is a rechargeable power tool battery pack that is usable with a variety of power tools (e.g., drills, screwdrivers, saws, or the like). The battery pack 50 is insertable into a cavity 318 (FIG. 4) formed in an end of the grip portion 78 substantially opposite the support portion 82. As shown in FIG. 2, the battery pack 50 is inserted along the grip axis 106 extending through the grip portion 78.

Referring to FIGS. 4 and 5, the battery pack 50 includes a battery casing 322 enclosing one or more battery cells, an outer housing 326 coupled to the casing 322, and a coupling mechanism. The battery casing 322 fits within the cavity 318 and supports receptacles 330 configured to engage and electrically connect to the battery terminals 70. The receptacles 330 and the casing 322 substantially enclose and cover the battery terminals 70 when the casing 322 is positioned within the cavity 318. However, the grip portion 78 does not include a cover or end cap such that, when the casing 322 is removed from the cavity 318, the battery terminals 70 are generally exposed to the surrounding environment.

The outer housing 326 surrounds the battery casing 322 and is positioned outside of the cavity 318 when the casing 322 is inserted into the grip portion 78. As shown in FIGS. 1-3, the outer housing 326 is generally shaped and sized to match the contours of the grip portion 78 such that, when the casing 322 is positioned within the cavity 318, the outer housing 326 defines a portion of the grip portion 78. That is, the outer housing 326 of the battery pack 50 mates with the upper and lower housings 54, 58 of the body 34 to generally extend the length of the grip portion 78.

The coupling mechanism of the battery pack 50 includes two actuators 334 and two tabs 338 to releasably secure the battery pack 50 to the body 34. In the illustrated embodiment, the actuators 334 and the tabs 338 are formed as a single piece with the outer housing 326. The tabs 338 engage corresponding recesses 340 (one of which is shown in FIG. 4). Due to the resiliency of the material forming the outer housing 326, the tabs 338 are normally biased away from the battery casing 322 to engage the recesses 340. Actuating (e.g., depressing) the actuators 334 moves the tabs 338 out of engagement with the recesses 340 such that the battery pack 50 may be pulled away from the body 34. This arrangement allows a user to quickly remove the battery pack 50 from the device for recharging or replacement without the use of tools. In addition, the illustrated coupling mechanism allows the battery pack 50 to be self-secured to the body 34 of the device 30 and does not require an additional cover and/or fastening member to hold the battery pack 50 within the cavity 318.

FIGS. 16A-17B illustrate two such battery packs 50A, 50B usable with the visual inspection device 30. The battery packs 50A, 50B are substantially similar to one another and to the battery pack 50 discussed above, and like parts have been given the same reference numbers plus an 'A' or 'B' designation.

The battery pack 50A illustrated in FIGS. 16A and 17A is a six-volt (6V) alkaline battery pack. The illustrated battery pack 50A includes four alkaline-based battery cells positioned within the battery casing 322A. In some embodiments, the battery pack 50A may include, for example, standard rechargeable AA batteries, AAA batteries, or the like positioned within the battery casing 322A. The alkaline battery pack 50A is operable to power the visual inspection device 30 for about five to ten hours of use.

The battery pack 50B illustrated in FIGS. 16B and 17B is a twelve-volt (12V) battery pack. The illustrated battery pack 50B may include three battery cells having, for example, a lithium (Li), lithium-ion (Li-ion), or other lithium-based chemistry. For example, the battery cells may have a chemistry of lithium-cobalt (Li—Co), lithium-manganese (Li—Mn) spinel, or Li—Mn nickel. In such embodiments, each battery cell may have a nominal voltage of about, for example, 3.6V, 4.0V, or 4.2V. In other embodiments, the battery cells may have a nickel-cadmium, nickel-metal hydride, or lead acid battery chemistry. In further embodiments, the battery pack 50B may include fewer or more battery cells, and/or each battery cell may have a different nominal voltage. The Li or Li-ion battery pack 50B is operable to power the visual inspection device 30 for about fifteen to twenty hours of use.

As shown in FIGS. 17A and 17B, an outer surface portion 342A, 342B of each battery casing 322A, 322B (e.g., the top surface in the drawings) has a unique contour. The outer surface portion 342A of the battery casing 322A shown in FIG. 17A is substantially inclined or sloped, while the outer surface portion 342B of the battery casing 322B shown in FIG. 17B is substantially planar. Providing two different contours to the outer surface portions 342A, 342B allows both battery packs 50A, 50B to be inserted into the cavity 318 of the visual inspection device 30, but prevents the battery packs 50A, 50B from being connected to and charged by an improper battery charger.

As mentioned above, in some embodiments, the flexible cable 38 may be connected to a cable extension 346 to increase the total length of the flexible cable 38. FIGS. 18-21 illustrate one embodiment of the cable extension 346. The illustrated cable extension 346 may be, for example, a three-foot extension positioned between the body 34 and the flexible cable 38 to increase the length of the flexible cable 38 from three feet to six feet. In some embodiments, multiple cable extensions 346 may be provided between the body 34 and the flexible cable 38 (e.g., three three-foot extensions to increase the total length of the flexible cable 38 by nine feet). In the illustrated embodiment, the cable extension 346 includes a first connector portion 350 (FIGS. 18 and 19) configured to couple to the stem connector portion 158 of the connecting assembly 154 (FIG. 9) and a second connector portion 354 (FIGS. 20 and 21) configured to couple to the cable connector portion 162 of the connecting assembly 154 (FIG. 10). The illustrated cable extension 346 is composed of substantially the same materials and has approximately the same outer diameter as the flexible cable 38 such that the cable extension 346 performs (e.g., bends) in a substantially similar manner to the flexible cable 38.

Figure 18:
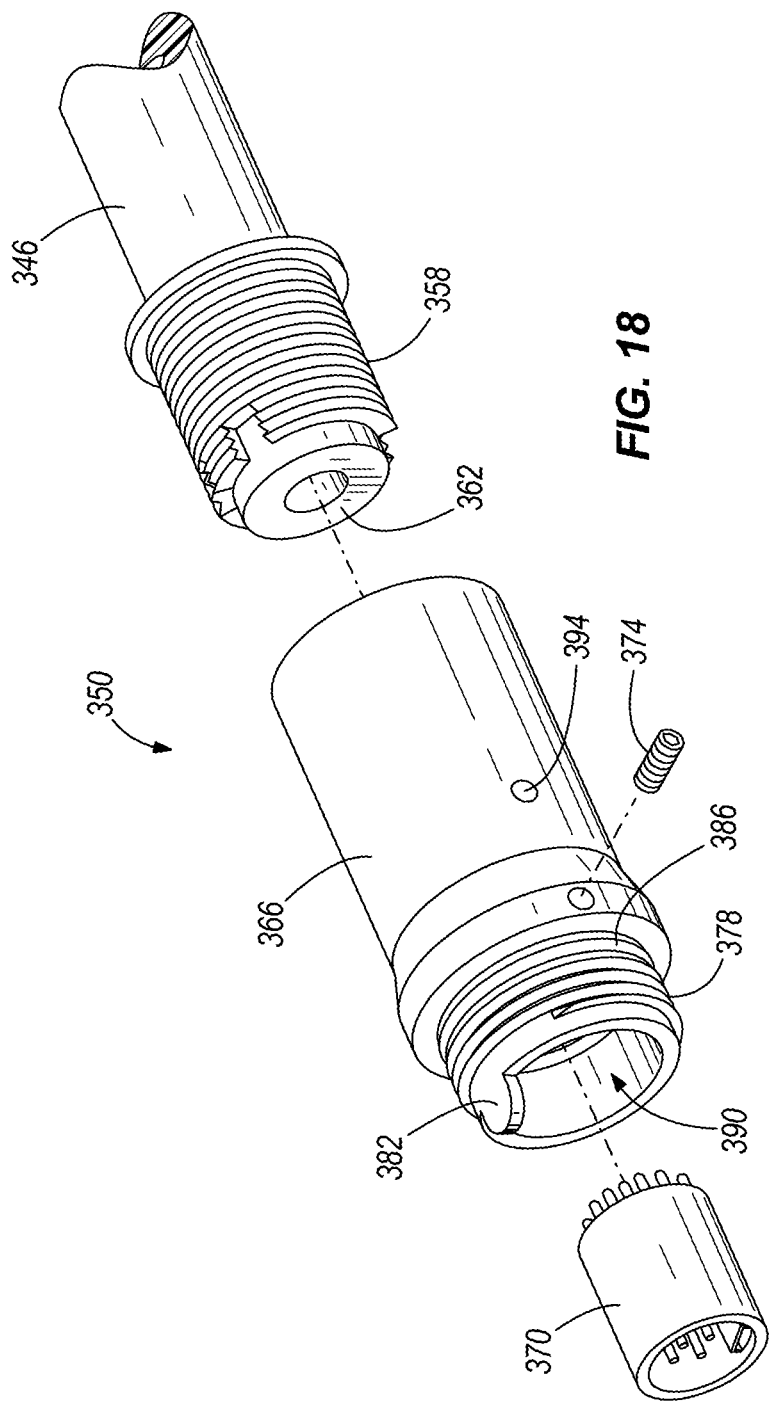
FIG. 18 is an exploded view of a first connector portion of an extension cable for use with the visual inspection device.
Figure 19:
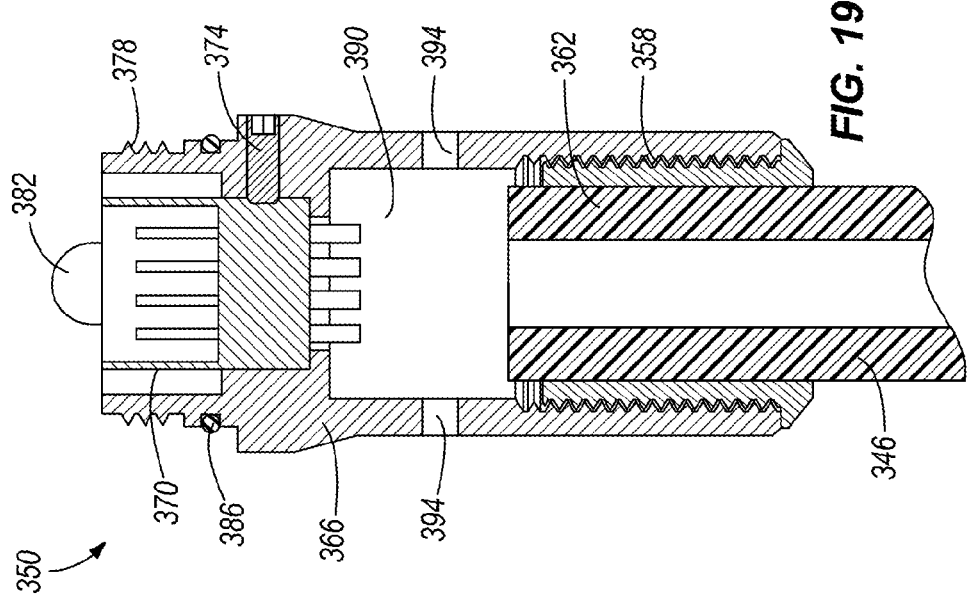
FIG. 19 is a cross-sectional view of the first connector portion of the extension cable of FIG. 18.

Referring to FIGS. 18 and 19, the illustrated first connector portion 350 includes an adaptor 358 securely mounted (e.g., press fit) on a first end portion 362 of the cable extension 346, a plug connector 366 threadably coupled to the adaptor 358, and an electrical connector 370, or din receptacle, positioned substantially within the plug connector 366. The illustrated electrical connector 370 is a 9-pin connector configured to mate with the electrical connector 370 of the stem connector portion 158 (FIG. 9) and is secured in place with a set screw 374. The illustrated plug connector 366 includes a threaded portion 378 configured to be engaged by the threaded portion 214 of the collar 174 (FIG. 9) to secure the cable extension 346 to the stem 130. The plug connector 366 also includes a tongue 382 configured to be received in the recess 222 formed in the stem 130 (FIG. 8) to inhibit rotation of the cable extension 346 relative to the stem 130. An elastomeric member 386 (e.g., an O-ring) is positioned adjacent to the threaded portion 378 of the plug connector 366 to help waterproof the first connector portion 350. In some embodiments, a cavity 390 in the plug connector 366 between the electrical connector 370 and the extension cable 346 may be filled through ports 394 with a potting compound to help waterproof the first connector portion 350 and secure the plug connector 366 and the electrical connector 370 in place.

Figure 20:
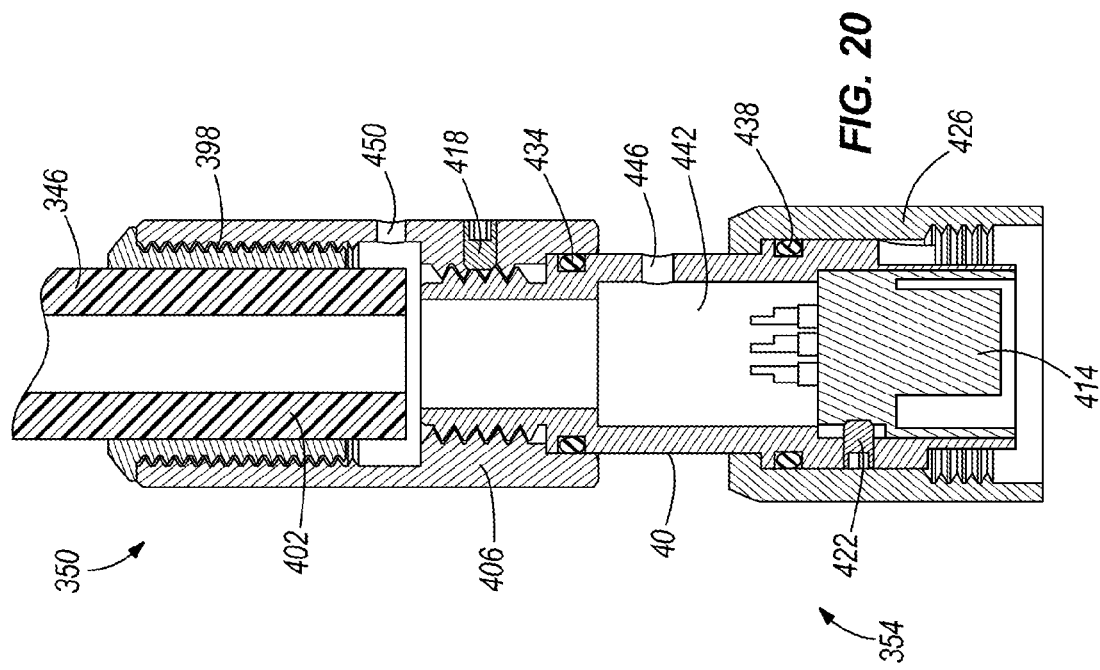
FIG. 20 is an exploded view of a second connector portion of the extension cable.
Figure 21:
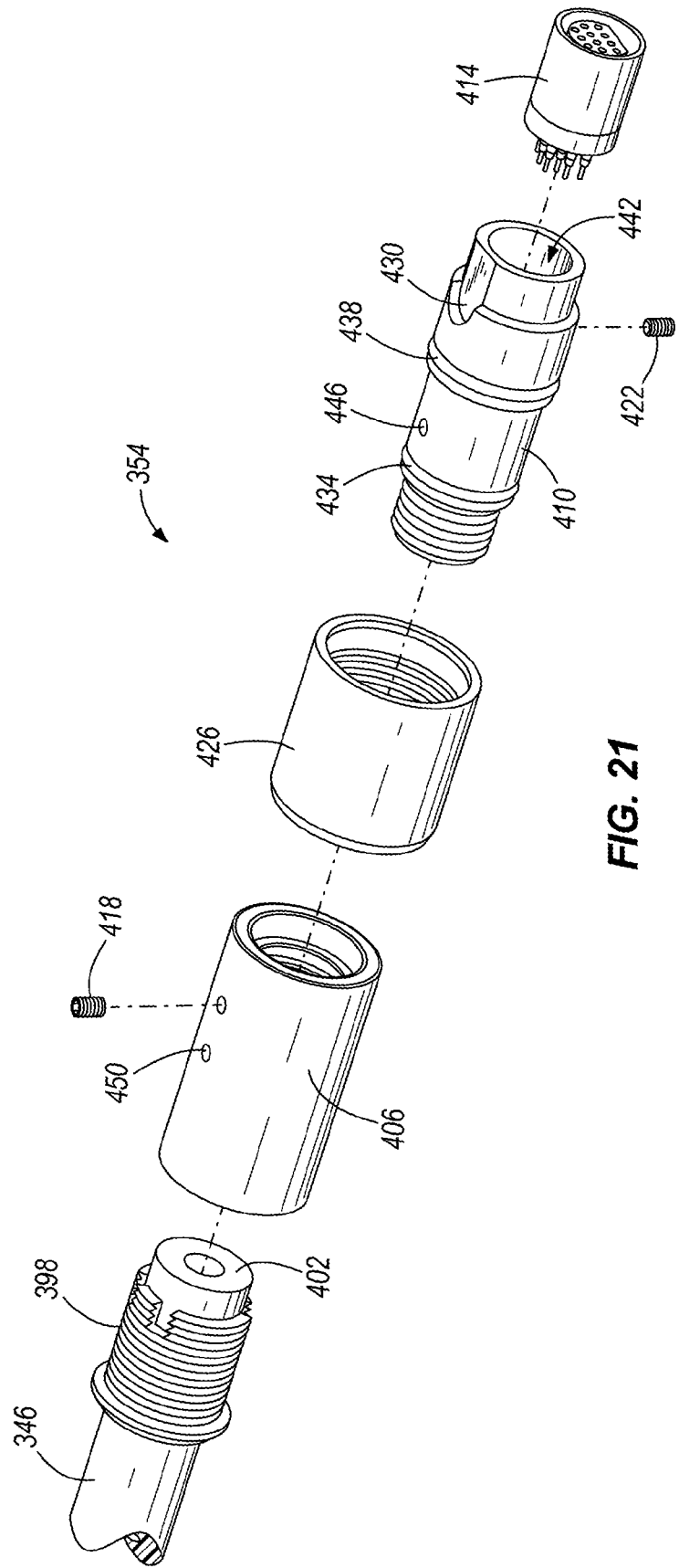
FIG. 21 is a cross-sectional view of the second connector portion of the extension cable of FIG. 20.

Referring to FIGS. 20 and 21, the second connector portion 354 includes an adaptor 398 securely mounted (e.g., press fit) on a second end portion 402 of the cable extension 346, an extension connector 406 threadably coupled to the adaptor 398, a receptacle connector 410 partially received in the extension connector 406, and an electrical connector 414, or din receptacle, positioned substantially in an end of the receptacle connector 410 opposite the extension connector 406. A set screw 418 extends through the extension connector 406 and engages the receptacle connector 410 to help secure the receptacle connector 410 relative to the extension connector 406. The illustrated electrical connector 414 is a 9-pin connector configured to mate with the electrical connector 202 of the cable connector portion 162 (FIG. 10) and is secured in place with a set screw 422.

The second connector portion 354 also includes a collar 426, or sleeve, slidably coupled to the receptacle connector 410 that engages the threaded portion 210 of the cable connector portion 162 (FIG. 10). The receptacle connector 410 includes a recess 430 configured to receive the tongue 218 on the plug connector 198 of the cable connector portion 162 (FIG. 8) to inhibit rotation of the flexible cable 38 relative to the cable extension 346. A first elastomeric member 434 (e.g., an O-ring) is positioned between the receptacle connector 410 and the extension connector 406, and a second elastomeric member 438 (e.g., an O-ring) is positioned between the receptacle connector 410 and the collar 426. The elastomeric members 434, 438 help waterproof the second connector portion 354 of the cable extension 346. In some embodiments, a cavity 442 in the receptacle connector 410 between the second end portion 402 of the cable extension 346 and the electrical connector 414 may be filled through ports 446, 450 with a potting compound to help waterproof the second connector portion 354 and secure the extension connector 406, the receptacle connector 410, and the electrical connector 414 in place.

Figure 22:
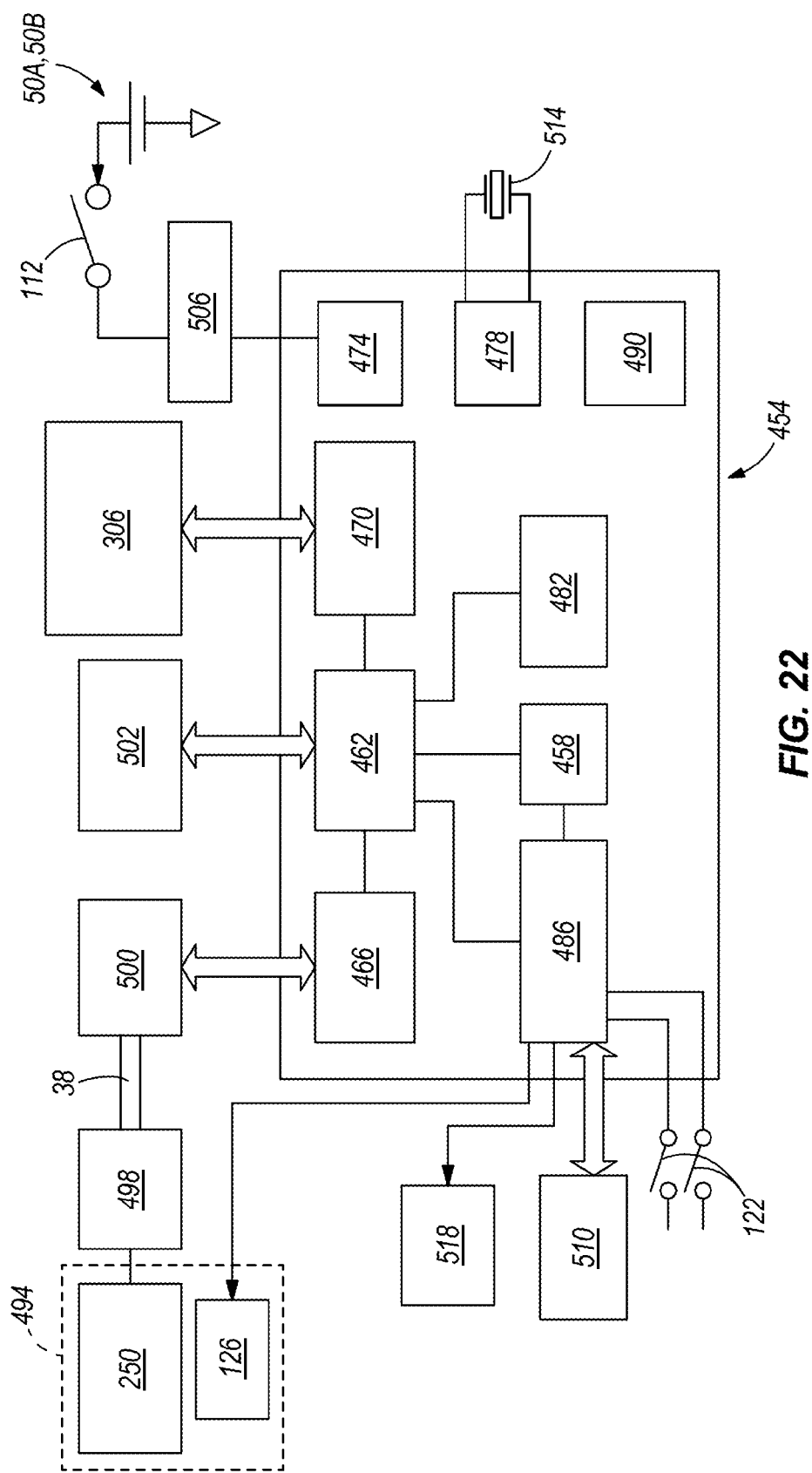
FIG. 22 is a schematic of a digital signal processor for use with the video inspection device.

As shown in FIG. 22, the video inspection device 30 includes a digital signal processor integrated circuit (DSP) 454 for controlling the device 30. In the illustrated embodiment, the DSP 454 is at least partially supported on the display control PCB 62 (FIG. 5). The DSP 454 includes, among other things, a central processing unit (CPU) 458, a memory management module 462, a video input module 466, a video output module 470, a power module 474, a clock generation module 478, a compression module 482, an interface unit (IFU) 486, and a real-time clock (RTC) module 490. The DSP 454 is connected to a plurality of other modules and devices, such as a camera module 494, a serializer/deserializer 498, 500, a volatile memory module 502, the LCD 306 (digital LCD (DLCD)), a power conditioning module 506, a non-volatile memory module 510, and an external crystal oscillator 514. The DSP 454 is configured to function as a digital still camera (DSC) and a digital video camcorder (DVC) device.

The CPU 458 includes memory and is capable of executing computer instructions fetched from the memory. The CPU 458 is also capable of retrieving an image or a video stored in memory. Additionally or alternatively, the CPU 458 is coupled to the volatile solid state memory 502, such as a synchronous dynamic random access memory (SDRAM) (4 MB) and the non-volatile solid state memory 510, such as a flash memory (16 MB). The SDRAM 502 is used for loading and executing computer program applications stored in the flash memory 510. The flash memory 510 is used for storing executable instructions (software code or application programs) and storing images or video. In some embodiments of the invention, the interface unit 486 connects additional external memory to the DSP 454.

The CPU 458 is also connected to the video input module 466 and the video output module 470 through the memory management module 462. The video input module 466 receives a digital signal from the camera module 494. The digital signal passes through the serializer 498 to produce one or more serial data streams which can be transmitted through one or more wires in the flexible cable 38. The serial data streams are deserialized in the deserializer 500 before the digital signal is sent to the video input module 466. Serializing a signal from the camera module 494 reduces the number of wires and signals required between the DSP 454 and the camera module 494 (for example, a cable reduction of 16:9 or less). The video output module 470 is coupled to the video input module 466 through the memory management module 462 and is connected to the LCD 306. The LCD 306 is, for example, a 2.4 inch thin film transistor (TFT) display (480× 240 resolution). In some embodiments of the invention, alternate types of LCDs are used. The LCD 306 can vary by pixel resolution or color representation methods. For example, in some embodiments, the LCD 306 uses 24-bit truecolor representation, which allows for over 16 million possible colors for each pixel of the LCD 306. The LCD 306 also includes an on-screen display of information. As mentioned above, the LCD 306 displays the battery life indicator 310 and the zoom indicator 314. In some embodiments, the LCD 306 may also display an LED brightness level indicator. In other embodiments of the invention, the LCD 306 displays additional or alternative information.

The memory management module 462 is coupled to the video input module 466, the video output module 470, the SDRAM 502, the flash memory 510 (through the IFU 486), the CPU 458, and the compression module 482. The memory management module 462 is configured to manage memory access requests from the CPU 458. The memory management module 462 is capable of managing physical and virtual memory addresses, protecting memory, controlling a cache, and arbitrating access to one or more data buses. The memory management module 462 is configured to, among other things, provide memory space to enable one or more software applications or instructions to be executed concurrently and to share memory space between different processes within the DSP 454. In some embodiments of the invention, the memory management module 462 is coupled to additional modules within the DSP 454 and is capable of performing additional functions.

The compression module 482 is coupled to the memory management module 462 and is configured to reduce the quantity of data used to represent a video or an image. The compression module 482 uses, for example, video or image compression methods approved by the International Organization for Standardization (ISO), or the International Telecommunication Union Telecommunications Standardization Sector (ITU-T). The compression module 482 includes, for example, lossy type image compression and video compression algorithms.

The power module 474 is coupled to the power conditioning module 506 and receives a regulated voltage from a voltage source such as, for example, the 6V alkaline battery pack 50A or the 12V lithium-ion battery pack 50B. In other embodiments of the invention, different types of batteries are used. Optionally, the video inspection device 30 includes a wired power solution (e.g. a power cable and plug). The power conditioning module 506 is, for example, a voltage regulator which receives a DC voltage of between approximately 5 Volts and approximately 15 Volts. The power conditioning module 506 reduces the input DC voltage to a constant level (±3%) required by the DSP 454. For example, the DSP 454 may require a constant voltage of 5 Volts or a constant voltage of 3.6 Volts. The first actuator 112, or ON/OFF switch, is connected between the power conditioning module 506 and the voltage source (e.g. the battery pack 50A, 50B). When the ON/OFF switch 112 is in an ON-position, the power conditioning module 506 provides a regulated voltage to the DSP 454. When the ON/OFF switch 112 is in an OFF-position, no energy is supplied to the power conditioning module 506 or the DSP 454.

The clock generation module 478 provides one or more timing signals required by the DSP 454. In some embodiments, the clock generation module 478 uses a phase lock loop (PLL) that includes a voltage controlled oscillator for producing one or more clock frequencies required by the DSP 454. The external crystal oscillator 514 is connected to a first input and a second input of the clock generation module 478 to provide an external reference frequency of, for example, 13.5 MHz. In other embodiments, different types of oscillators and different reference frequencies are used.

The camera module 494 is coupled to the serializer 498 and includes, among other things, the camera unit 250 and the light source 126. As discussed above, the camera unit 250 is, for example, a CMOS sensor (a 300K pixels, 30 frames-per-second camera sensor) such as an active pixel sensor or an analog CCD image sensor. In some embodiments, the camera module 494 is configured to automatically focus on an object in an image and to automatically control exposure and white balance in digital images and digital video.

The DSP 454 is also coupled to additional input/output ports 518 (I/O port), such as, for example, a universal serial bus (USB) port. The USB port 518 connects the DSP 454 to an external device such as an external USB memory device, a monitor, or a computer.

Although the invention has been described in detail with reference to preferred embodiments, variations and modifications exist within the scope and spirit of one or more independent aspects of the invention as described. Various features and advantages of the invention are set forth in the following claims.

What is claimed is:

1. A visual inspection device comprising:
 a body including a support portion and a grip portion extending from the support portion, the grip portion defining a first axis;
 a flexible cable including a first end portion coupled to the body and a second end portion, the first end portion defining a second axis;
 a camera assembly coupled to the second end portion of the flexible cable, the camera assembly including an image sensor, the image sensor operable to transmit image data through the flexible cable;
 a display supported by the support portion of the body, the display electrically connected to the flexible cable to display images captured by the image sensor, the display defining a display plane;
 a battery terminal supported by the grip portion, the battery terminal being electrically connected to at least one of the image sensor and the display; and
 a rechargeable battery pack inserted into the grip portion along the first axis, the battery pack including a coupling mechanism configured to engage the body to releasably secure the battery pack to the body, a portion of the battery pack being engageable with the battery terminal, the battery terminal being generally exposed when the battery pack is not secured to the body, wherein the first axis and the display plane form a first angle, the second axis and the first axis form a second angle, and the second axis and the display plane form a third angle, wherein the coupling mechanism includes a first actuator, a first tab, a second actuator, and a second tab, the first tab configured to engage a first recess of the body, the second tab configured to engage a second recess of the body, and wherein actuating the first actuator moves the first tab out of engagement with the first recess and actuating the second actuator moves the second tab out of engagement with the second recess such that the battery pack can be disengaged from the body.

2. The visual inspection device of claim 1, wherein the flexible cable is removably coupled to the body.

3. The visual inspection device of claim 1, wherein the battery pack includes at least one battery cell and an outer housing, wherein the outer housing defines a portion of the body when the battery pack is coupled to the inspection device.

4. The visual inspection device of claim 3, wherein the battery cell is a lithium-ion battery cell.

5. The visual inspection device of claim 1, wherein the battery pack includes a receptacle, and wherein the receptacle receives the battery terminal to electrically connect the battery pack to the battery terminal.

6. The visual inspection device of claim 1, wherein the rechargeable battery pack includes an outer housing, and wherein the outer housing is shaped and sized to match the contours of the grip portion.

7. The visual inspection device of claim 1, wherein the display plane intersects the first axis at an acute angle.

8. The visual inspection device of claim 1, further comprising a processing unit configured to receive image data from the image sensor.

9. The visual inspection device of claim 8, wherein the processing unit is connected to an external memory device.

10. A system of electrical devices comprising:
a visual inspection device, the visual inspection device including
a body including a support portion and a grip portion extending from the support portion, the grip portion defining a first axis,
a flexible cable including a first end portion coupled to the body and a second end portion, the first end portion defining a second axis,
a camera assembly coupled to the second end portion of the flexible cable, the camera assembly including an image sensor, the image sensor operable to transmit image data through the flexible cable,
a display supported by the support portion of the body, the display electrically connected to the flexible cable to display images captured by the image sensor, the display defining a display plane, and
a battery terminal being electrically connected to at least the display,
wherein the first axis intersects the display plane at a first angle, the second axis intersects the first axis at a second angle, and the second axis intersects the display plane at a third angle; and
a removable and rechargeable battery pack inserted into the grip portion along the first axis, the battery pack configured to be coupled to and provide power to the inspection device, the removable and rechargeable battery pack including a coupling mechanism that is configured to engaged the body to releasably secure the battery pack to the body, a portion of the battery pack being engageable with the battery terminal, the coupling mechanism including a first actuator, a first tab, a second actuator, and a second tab, the first tab configured to engage a first recess of the body, the second tab configured to engage a second recess of the body,
wherein actuating the first actuator moves the first tab out of engagement with the first recess and actuating the second actuator moves the second tab out of engagement with the second recess such that the battery pack can be disengaged from the body.

11. The system of claim 10, wherein the flexible cable is removably coupled to the body.

12. The system of claim 11, wherein the rechargeable battery pack includes an outer housing, and wherein the outer housing is shaped and sized to match the contours of the grip portion.

13. The system of claim 12, wherein the rechargeable battery pack further includes a casing, and wherein the outer housing is coupled to the casing.

14. The system of claim 10, wherein the battery pack includes at least one battery cell and an outer housing, wherein the outer housing defines a portion of the body when the battery pack is coupled to the inspection device.

15. The system of claim 14, wherein the battery cell is a lithium-ion battery cell.

16. The system of claim 10, further comprising a power tool.

17. The system of claim 16, wherein the removable and rechargeable battery pack is also configured to be coupled to and provide power to the power tool.

18. The system of claim 17, wherein the power tool is selected from the group consisting of a drill, a screwdriver, and a saw.

19. The system of claim 10, wherein the visual inspection device further includes a processing unit configured to receive image data from the image sensor.

20. The system of claim 19, wherein the processing unit is connected to an external memory device.

* * * * *